United States Patent [19]

Reim et al.

[11] Patent Number: 5,122,457
[45] Date of Patent: Jun. 16, 1992

[54] EXPRESSION SYSTEMS UTILIZING BACTERIOPHAGE T7 PROMOTERS, GENE SEQUENCES, AND T7 RNA POLYMERASE

[75] Inventors: Richard L. Reim, Edison; Satwant K. Narula, West Caldwell; Michael J. Ryan, West Milford; Paul J. Leibowitz, Hackensack, all of N.J.

[73] Assignee: Schering Corporation, Kenilworth, N.J.

[21] Appl. No.: 423,839

[22] Filed: Oct. 19, 1989

[51] Int. Cl.$^5$ .............. C12P 21/00; C12N 9/10; C12N 1/21; C12N 15/54
[52] U.S. Cl. ................... 435/69.1; 435/69.52; 435/91; 435/172.3; 435/194; 435/252.3; 435/252.33; 435/320.1; 536/27; 935/3; 935/33; 935/38
[58] Field of Search .......... 435/320.1, 172.3, 252.3, 435/69.1, 252.33, 194; 536/27

[56] References Cited

U.S. PATENT DOCUMENTS 4,892,743  1/1990  Leibowitz et al. ............ 435/69.51
4,952,496  8/1990  Studier et al. ............... 435/194

FOREIGN PATENT DOCUMENTS 178863  4/1986  European Pat. Off. ......... 435/69.1
8810307  12/1988  PCT Int'l Appl. ............. 435/69.1

OTHER PUBLICATIONS

Lehninger (1982), Principles of Biochemistry (Worth Pub, N.Y.) pp. 226-229, 897.
Muller et al. (1988), Biochemistry, vol. 27, pp. 5763-5771.
Manlatis et al. (1982), Molecular Cloning, pp. 412-413.
Backman et al., Cell 13:65 (1978).
Davanloo et al., Proc. Natl. Acad. Sci. U.S.A. 81:2035 (1984).
Dunn et al., J. Mol. Biol. 166:477 (1983).
McAllister et al., J. Mol. Biol. 153:527 (1981).
Stahl et al., J. Mol. biol. 148:481 (1981).
Tabor et al., Proc. Natl. Acad. Sci. U.S.A. 82:1074 (1985).

Primary Examiner—Richard A. Schwartz
Assistant Examiner—Richard M. Lebovitz
Attorney, Agent, or Firm—James R. Nelson; Norman C. Dulak

[57] ABSTRACT

Expression systems which utilize bacteriophage T7 RNA mutant polymerases and promoter regions are provided by this invention. These systems are utilized to produce large quantities of useful polypeptides and proteins.

33 Claims, 15 Drawing Sheets

```
ATG AAC ACG ATT AAC ATC GCT AAG AAC GAC TTC TCT GAC ATC  42
GAA CTG GCT GCT ATC CCG TTC AAC ACT CTG GCT GAC CAT TAC  84
GGT GAG CGT TTA GCT CGC GAA CAG TTG GCC CTT GAG CAT GAG 126
TCT TAC GAG ATG GGT GAA GCA CGC TTC CGC AAG ATG TTT GAG 168
CGT CAA CTT AAA GCT GGT GAG GTT GCG GAT AAC GCT GCC GCC 210
AAG CCT CTC ATC ACT ACC CTA CTC CCT AAG ATG ATT GCA CGC 252
ATC AAC GAC TGG TTT GAG GAA GTG AAA GCT AAG CGC GGC AAG 294
CGC CCG ACA GCC TTC CAG TTC CTG CAA GAA ATC AAG CCG GAA 336
GCC GTA GCG TAC ATC ACC ATT AAG ACC ACT CTG GCT TGC CTA 378
ACC AGT GCT GAC AAT ACA ACC GTT CAG GCT GTA GCA AGC GCA 420
ATC GGT CGG GCC ATT GAG GAC GAG GCT CGC TTC GGT CGT ATC 462
CGT GAC CTT GAA GCT AAG CAC TTC AAG AAA AAC GTT GAG GAA 504
CAA CTC AAC AAG CGC GTA GGG CAC GTC TAC AAG AAA GCA TTT 546
ATG CAA GTT GTC GAG GCT GAC ATG CTC TCT AAG GGT CTA CTC 588
GGT GGC GAG GCG TGG TCT TCG TGG CAT AAG GAA GAC TCT ATT 630
CAT GTA GGA GTA CGC TGC ATC GAG ATG CTC ATT GAG TCA ACC 672
GGA ATG GTT AGC TTA CAC CGC CAA AAT GCT GGC GTA G        709
```

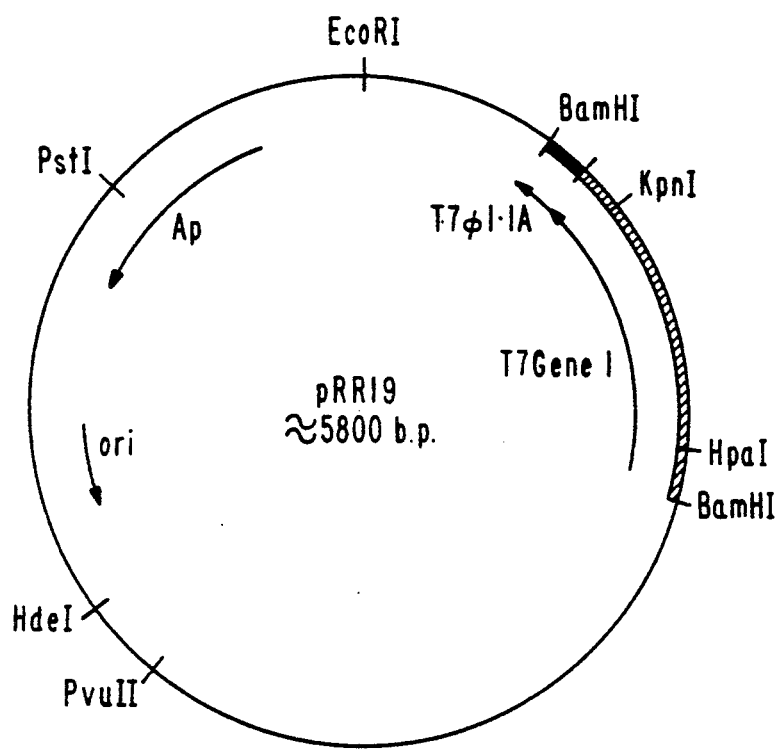
DIAGRAM OF pRR19  FIG. 1
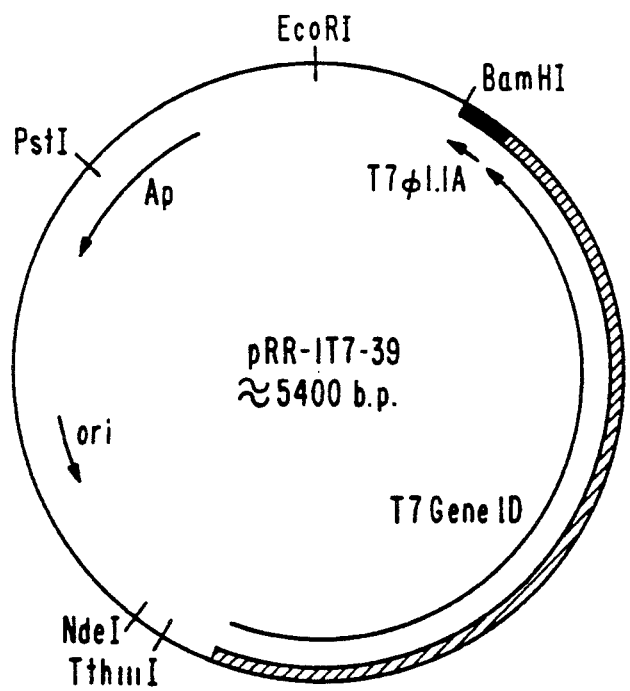
DIAGRAM OF pRR-1T7-39  FIG. 2

CONSTRUCTION OF p804-RI lac

CONSTRUCTION OF pRR-1T7L-3

CLONING OF T7 Gene 2

DIAGRAM OF pRR-2T7-35

DERIVATION OF pRR-1B-2T7 FROM pRR-2T7-35

Insertion of BamHI linkers into NdeI site of pRR-1B-2T7

Construction of pRR-1T7G2 lac 7

DIAGRAM OF pAC-1T7G2-78

CLONING OF THE T7 GENE 10 PROMOTER

Cloning the T7 Gene 10 promoter adjacent to the IFN-Alpha 2 gene

CONSTRUCTION OF pAC-φ10IF-2

Bal 31 digestion of the region between the lac promoter and T7 Gene I

Construction of pRRB20IF-23

FIG. 16

```
ATG AAC ACG ATT AAC ATC GCT AAG AAC GAC TTC TCT GAC ATC   42
GAA CTG GCT GCT ATC CCG TTC AAC ACT CTG GCT GAC CAT TAC   84
GGT GAG CGT TTA GCT CGC GAA CAG TTG GCC CTT GAG CAT GAG  126
TCT TAC GAG ATG GGT GAA GCA CGC TTC CGC AAG ATG TTT GAG  168
CGT CAA CTT AAA GCT GGT GAG GTT GCG GAT AAC GCT GCC GCC  210
AAG CCT CTC ATC ACT ACC CTA CTC CCT AAG ATG ATT GCA CGC  252
ATC AAC GAC TGG TTT GAG GAA GTG AAA GCT AAG CGC GGC AAG  294
CGC CCG ACA GCC TTC CAG TTC CTG CAA GAA ATC AAG CCG GAA  336
GCC GTA GCG TAC ATC ACC ATT AAG ACC ACT CTG GCT TGC CTA  378
ACC AGT GCT GAC AAT ACA ACC GTT CAG GCT GTA GCA AGC GCA  420
ATC GGT CGG GCC ATT GAG GAC GAG GCT CGC TTC GGT CGT ATC  462
CGT GAC CTT GAA GCT AAG CAC TTC AAG AAA AAC GTT GAG GAA  504
CAA CTC AAC AAG CGC GTA GGG CAC GTC TAC AAG AAA GCA TTT  546
ATG CAA GTT GTC GAG GCT GAC ATG CTC TCT AAG GGT CTA CTC  588
GGT GGC GAG GCG TGG TCT TCG TGG CAT AAG GAA GAC TCT ATT  630
CAT GTA GGA GTA CGC TGC ATC GAG ATG CTC ATT GAG TCA ACC  672
GGA ATG GTT AGC TTA CAC CGC CAA AAT GCT GGC GTA G        709
```

EXPRESSION SYSTEMS UTILIZING BACTERIOPHAGE T7 PROMOTERS, GENE SEQUENCES, AND T7 RNA POLYMERASE

TECHNICAL FIELD

This invention relates to recombinant DNA sequences and vectors containing bacteriophage T7 promoters, inducible bacterial or viral promoters, genes encoding mutant T7 RNA polymerases, and heterologous genes, and to methods for efficiently expressing heterologous genes using such vectors in microbial expression systems.

BACKGROUND OF THE INVENTION

It is now possible through the techniques of genetic engineering to cause a host cell to produce "heterologous" polypeptides, i.e., polypeptides which are not naturally produced by that species of cell. A variety of mammalian polypeptides have been produced in *E. coli* such as somatostatin, described by Itakura et al., Science 198:1056 (1977); the component A and B chains of human insulin, disclosed by Goeddel et al., Proc. Natl. Acad. Sci. USA 76:106 (1979); human growth hormone, disclosed by Goeddel et al., Nature 281:411 (1980); human fibroblast interferon, disclosed by Goeddel et al., Nucleic Acids Res. 8:4057 (1980); and human serum albumin, as disclosed by Lawn, et al., Nucleic Acids Res. 9:6103 (1981).

In the application of current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in a segment of foreign DNA that is to be inserted, the two DNA molecules may be covalently linked by an enzyme known as a ligase. General methods for the preparation of such recombinant DNA molecules have been described by Cohen et al. [U.S. Pat. No. 4,237,224], Collins et al. [U.S. Pat. No. 4,304,863] and Maniatis et al. [Molecular Cloning: A Laboratory Manual, 1982, Cold Spring Habor Laboratory].

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* as a host organism, because it is compatible with a wide range of recombinant plasmids. Depending upon the vector/host cell system used, the recombinant DNA molecule is introduced into the host by transformation, transduction or transfection.

Detection of the presence of recombinant plasmids in host cells may be conveniently achieved through the use of plasmid marker activities such as antibiotic resistance. For example, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity at a site where the selected restriction endonuclease makes its cut and the foreign gene sequence is inserted. Host cells containing the proper recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid called a promoter for DNA transcription.

Transcription of the gene into mRNA is instituted when an enzyme known as RNA polymerase contacts and interacts with the promoter sequence, thereafter moving along the gene and causing the synthesis of a mRNA molecule which is specified by the gene. The mRNA is thereafter translated into a specific polypeptide by cellular constituents, such as ribosomes, transfer RNAs, etc.

A variety of promoter sequences have been used to promote the expression of foreign or heterologous genes (i.e., genes not normally present) in *E. coli*, such as the lac promoter, Backman et al., Cell 13:65 (1978); the trp promoter, Hallewell et al., Gene 9:27 (1980); and the phage lambda $P_L$ promoter, Bernard et al., Gene 5:59 (1979).

A variety of gene promoter/operator (po) systems are "inducible"; i.e., their activity can be varied substantially by the presence or absence of a certain substance or condition. For example, the lac promoter system of *E. coli* has a relatively low level of activity in the absence of lactose. In this condition, it is said to be repressed. In the presence of an inducer such as lactose itself or isopropyl-$\beta$-D-thiogalactoside (IPTG), however, the lac promoter system becomes derepressed and causes a high level of transcription of the gene sequence adjoining the promoter. See, e.g., J. Miller and W. Reznikoff, *The Operon* 2d Edition, Cold Spring Harbor Laboratory, New York (1982). Other inducible promoter systems include e.g., the trp promoter (which has relatively low activity if an excess of tryptophan is present and higher activity if a low concentration of tryptophan or 3-betaindolylacrylic acid is present; see Hallewell et al., supra), and the phage lambda $P_L$ promoter (which has a relatively low level of activity at about 30° C. and higher activity at 41° C. in the presence of a temperature-sensitive mutant lambda repressor; see Bernard, supra).

The promoter regions present in the DNA of bacteriophage T7 are of particular interest since bacterial cells infected by this bacteriophage almost immediately begin to produce only T7 bacteriophage polypeptides, to the virtual exclusion of the host cell's own requirements. This action is in large measure a consequence of a very strong interaction between the bacteriophage T7 promoters and the T7 RNA polymerase. Bacteriophage T7 DNA is also known to code for a protein kinase which inactivates *E. coli* RNA polymerase by phosphorylation, thereby reducing transcription of *E. coli* DNA. It is because of these two factors that the protein synthesizing machinery of *E. coli* is directed almost exclusively to the production of bacteriophage protein shortly after infection.

It would, therefore, be very useful if the methods utilized by bacteriophage T7 to exclusively direct synthesis of bacteriophage-required proteins could be harnessed to direct the synthesis of polypeptides which are desired for medical, diagnostic, research, and other purposes.

A suggestion of the use of bacteriophage T7 promoters to direct the transcription of a cloned gene in bacteria is contained in McAllister et al., J. Mol. Biol. 153:527 (1981). This reference postulates that the T7 RNA polymerase which would be required to initiate the T7 promoter directed transcription would have to be supplied to the cell by infection or from the cloned T7 polymerase gene. The reference is silent as to any specific method for achieving this result.

Supplying T7 RNA polymerase by infection would not be practical, since the enzyme is produced only briefly during infection and does not accumulate to high levels. Furthermore, T7 bacteriophage infection would be accompanied by natural competition of T7 RNA polymerase for the cloned gene promoter and promoter regions present in the bacteriophage DNA itself, and the infected cells would lyse within a short period of time.

The cloning and expression of the gene for T7 RNA polymerase (T7 Gene 1) is reported in a later paper [Davanloo et al., Proc. Natl. Acad. Sci. USA 81:2035 (1984)]. The authors caution, however, that the presence of any T7 promoters in a plasmid containing T7 Gene 1 in the same orientation as the T7 promoters would have to be scrupulously avoided. They theorized that T7 RNA polymerase, by transcribing completely around such a plasmid would be able to direct the synthesis of its own mRNA from the cloned fragment that contained both the promoter and the intact T7 Gene 1. Such a construction, they believe, would lead to an autocatalytic increase both in the level of T7 RNA polymerase and in the rate of transcription of the plasmid; a condition which they say would almost certainly be lethal to the cell.

Davanloo et al. state that a single molecule of active T7 RNA polymerase would potentially be sufficient to trigger this response so such a construction, i.e., a plasmid containing both a T7 promoter region and the T7 RNA polymerase gene, would be stable only if there was absolutely no expression of the cloned T7 RNA polymerase gene. This situation, they conclude, may be difficult or impossible to achieve. These authors, therefore, utilized a bacterial promoter sequence to direct the transcription of the T7 Gene 1; but were very careful to be sure that the plasmid construct did not contain an intact T7 promoter region. This is complicated to achieve since the bacteriophage DNA has no conveniently located restriction sites that will permit the ready isolation of a fragment which contains all of the T7 Gene 1 coding sequence without any promoter region.

Finally, Davanloo et al. state that it is unlikely that a sequence containing both the T7 Gene 1 translatable coding sequence and a T7 promoter region could be cloned on the same plasmid. Their attempt to place a promoter for T7 RNA polymerase into a plasmid along with the T7 Gene 1 produced only arrangements in which the promoter directed transcription opposite to the direction needed to transcribe the polymerase gene.

Thus, the art appreciates the potential benefits of placing a foreign gene under the control of a T7 phage promoter. To date such a convenient non-lethal method for providing the T7 RNA polymerase to a system comprising a T7 promoter does not exist. The present invention provides a solution to this problem.

SUMMARY OF THE INVENTION

This invention provides novel DNA sequences, recombinant vectors and methods for the efficient expression of heterologous genes in bacterial expression systems. More particularly, this invention provides DNA sequences comprising a bacteriophage T7 promoter linked in correct reading frame to a gene encoding a desired heterologous protein or polypeptide. Preferably, the T7 promoter used is a class III promoter, most preferably a $\phi 10$ promoter.

This invention further provides DNA sequences comprising an inducible promoter linked in correct reading frame to a gene encoding a mutant bacteriophage T7 RNA polymerase which is capable of binding to a T7 promoter and carrying out transcription without being lethal to a bacterial host expressing the gene. In one embodiment of the invention, the gene contains one or more base deletions occurring between bases corresponding to bases 3809 and 3877 of a wild-type T7 RNA polymerase gene, which deletion causes early polypeptide chain termination. The inducible promoter can be of bacterial or viral origin, including but not limited to the lac or lambda $P_L$ promoter.

Also provided are recombinant vectors comprising a vector and a DNA sequence comprising a bacteriophage T7 promoter operatively linked to a gene encoding a desired heterologous protein or polypeptide, which recombinant vectors are capable of directing expression of the gene in a host bacterium. As used herein, "operatively linked" means that the gene is in correct reading frame with the promoter, and transcription initiates at the promoter and carries on through the gene, until a termination codon is reached.

This invention still further provides recombinant vectors comprising:

(a) a vector, and (b) a DNA sequence comprising an inducible promoter operatively linked to a gene encoding a mutant bacteriophage T7 RNA polymerase which is capable of binding to a T7 promoter and carrying out transcription without being lethal to a bacterial host expressing the gene, which recombinant vectors are capable of directing expression of the gene in a host bacterium.

In some embodiments of this invention, the T7 promoter/heterologous polypeptide or protein gene and inducible promoter/mutant RNA polymerase gene are in separate recombinant vectors; in others, they are combined in a single vector. When the two genes are present in one vector, the direction of transcription of the gene about the vector can be the same or opposite.

This invention still further provides transformed bacteria containing the above-mentioned recombinant vectors, methods for producing the desired polypeptides or proteins which employ such transformants, and mutant bacteriophage T7 RNA polymerases which are capable of binding to a T7 promoter and carrying out transcription without being lethal to bacterial hosts expressing genes encoding the polymerases.

BRIEF DESCRIPTION OF THE FIGURES

This invention can be more readily understood by reference to the accompanying figures, in which:

FIG. 1 shows the structure of pRR19 containing the cloned 1136 base pair T7 DNA fragment encoding the carboxy-terminal sequence.

FIG. 2 shows the structure of pRR-1T7-39 which contains the entire coding sequence of the mutant T7

RNA polymerase gene and the T7 1.1A promoter sequence.

Figure 3:
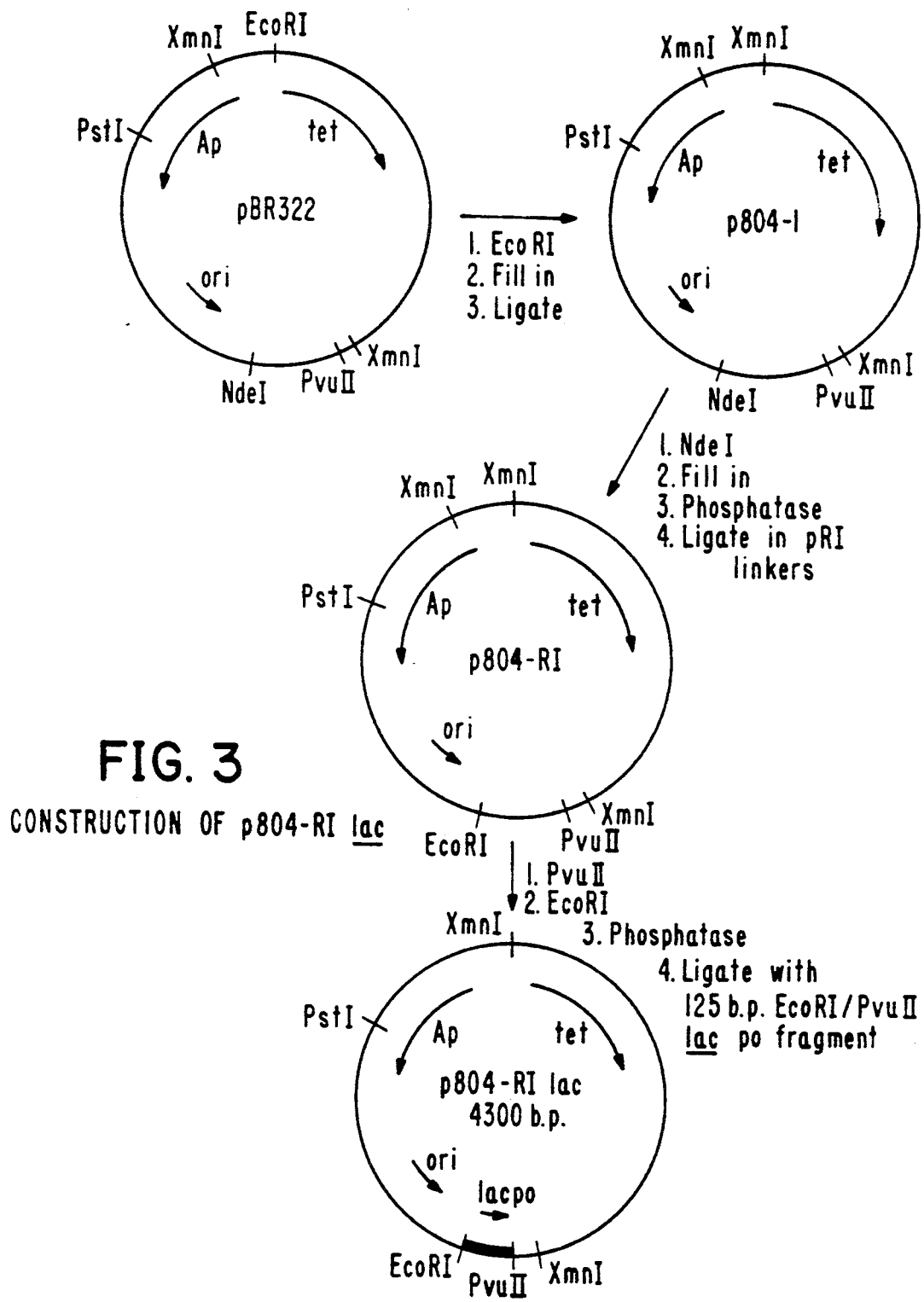

FIG. 3 shows schematically the steps taken to clone the lac promoter sequence. Two restriction enzyme sites in pBR322 were changed. The Eco RI site was filled in and then religated creating an XmnI site resulting in p804-1. Subsequently in p804-1, the NdeI site was filled in and an Eco RI linker sequence was ligated into the site creating p804-RI. The lac promoter sequence, which existed as an EcoRI/PvuII fragment, could then be cloned into p804-RI. The resultant plasmid, p804-RI lac is shown and has the lac promoter sequence oriented in the counter-clockwise direction.

Figure 4:
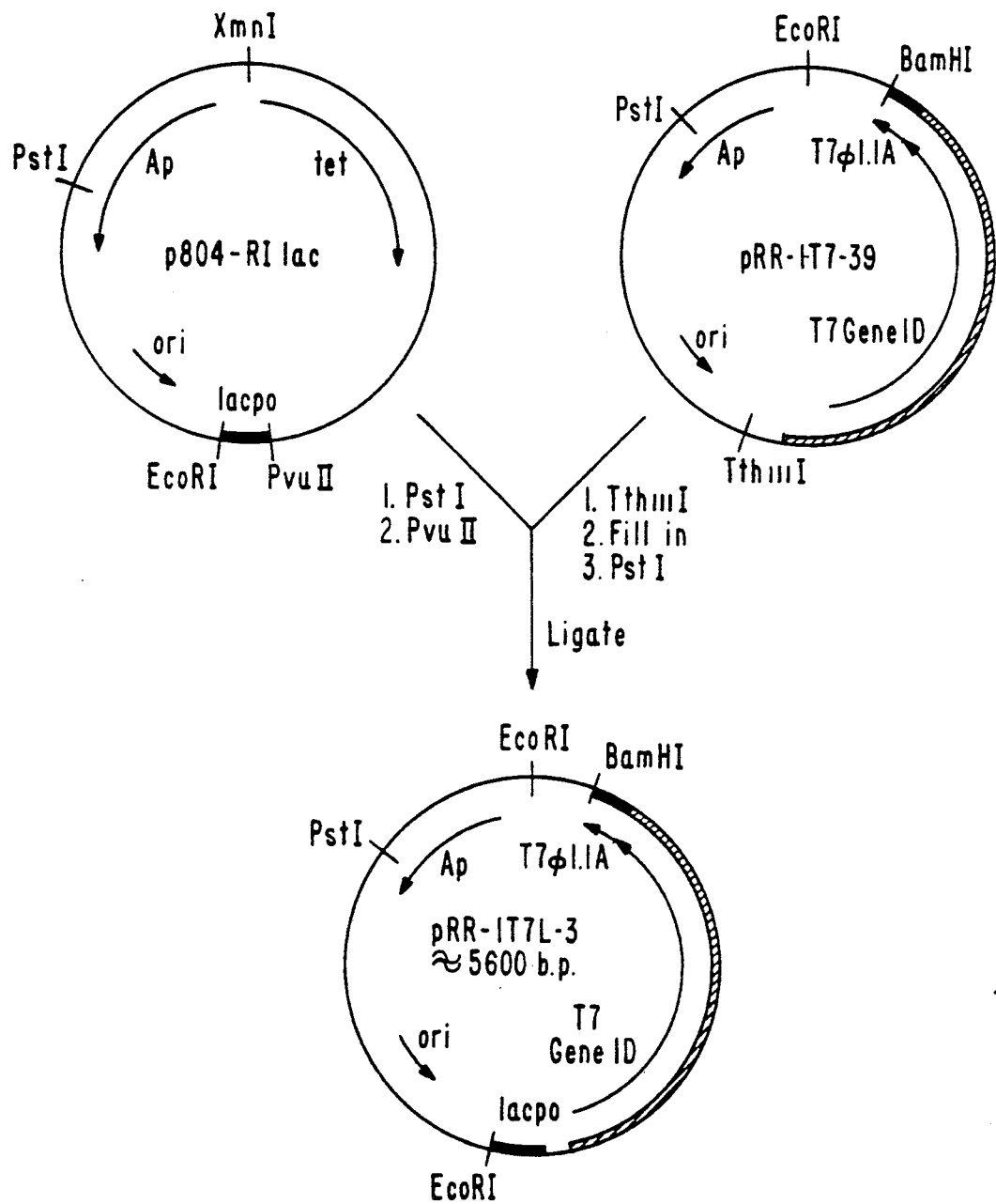

FIG. 4 shows the construction of a plasmid containing the mutant T7 RNA polymerase gene under the control of the lac promoter operator sequence.

Figure 5:
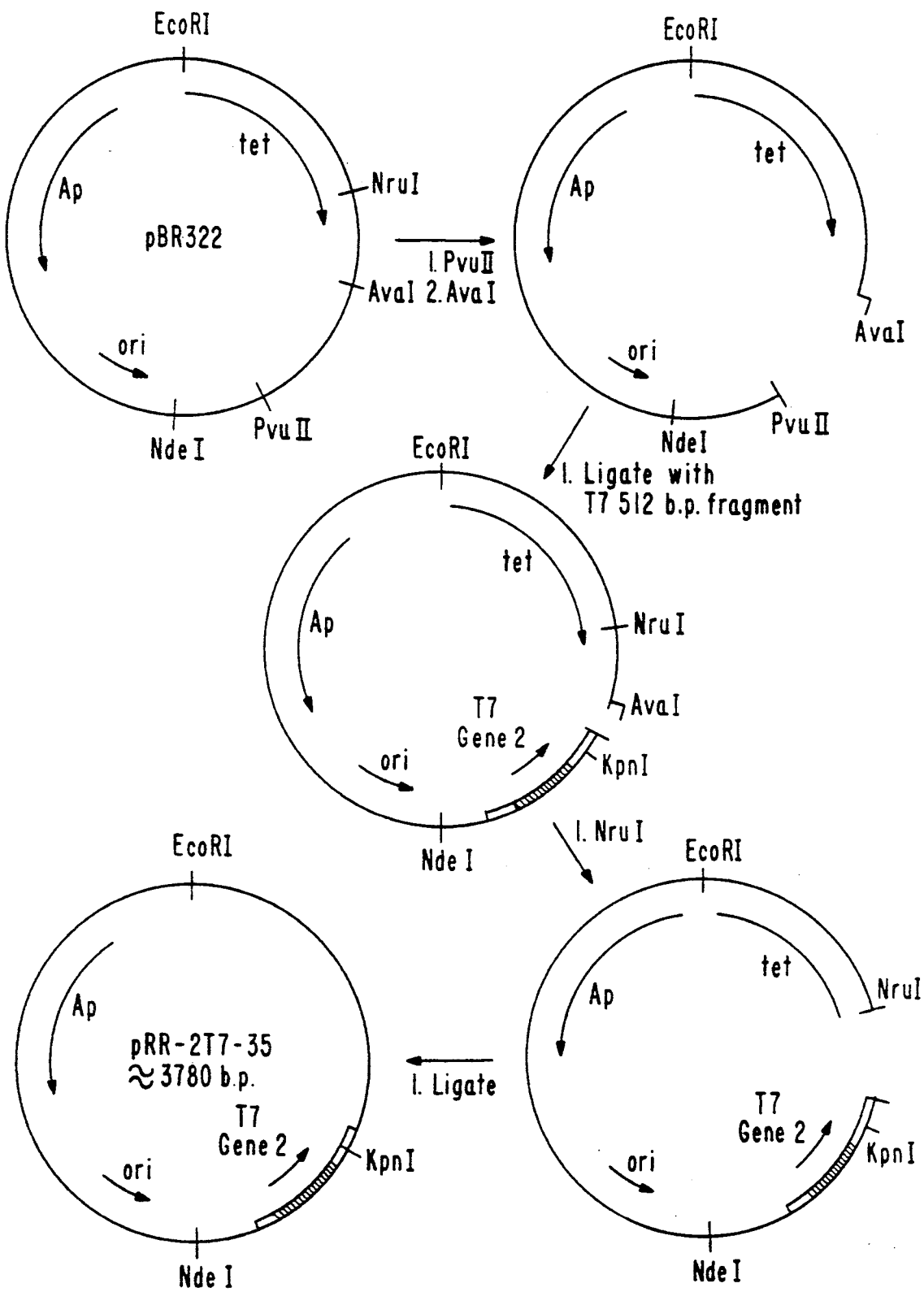

FIG. 5 shows the stepwise procedure used to clone the 512 base pair fragment encoding the T7 Gene 2 sequence into pBR322.

Figure 6:
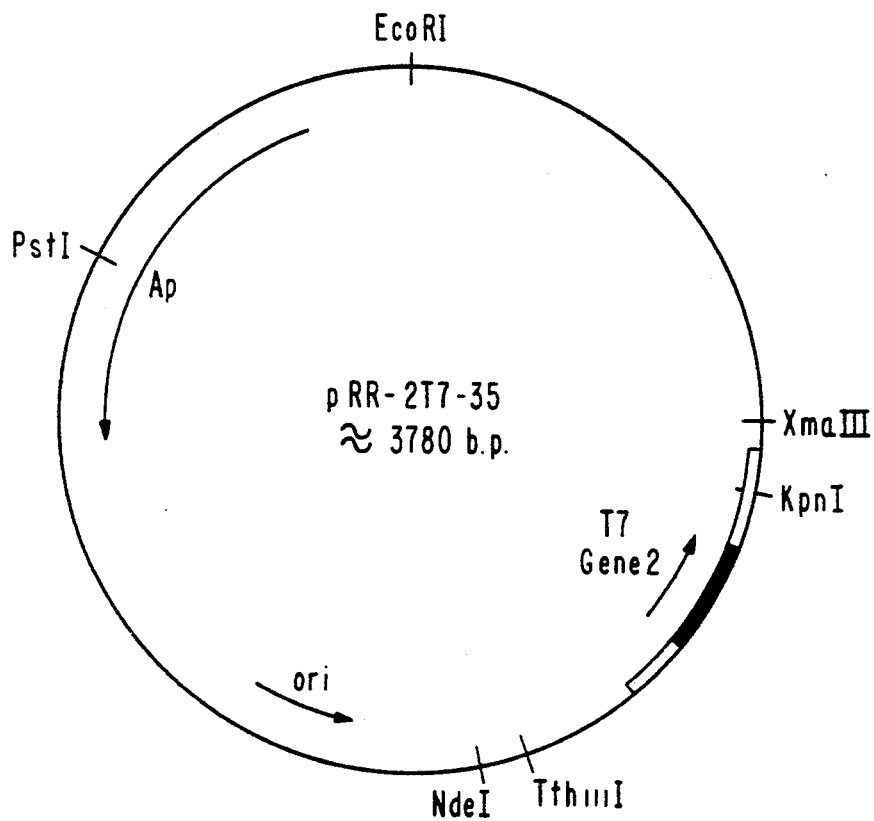

FIG. 6 depicts the structure of pRR-2T7-35. The cloned fragment was identified and the orientation deduced using the restriction enzyme site KpnI as a marker.

Figure 7:
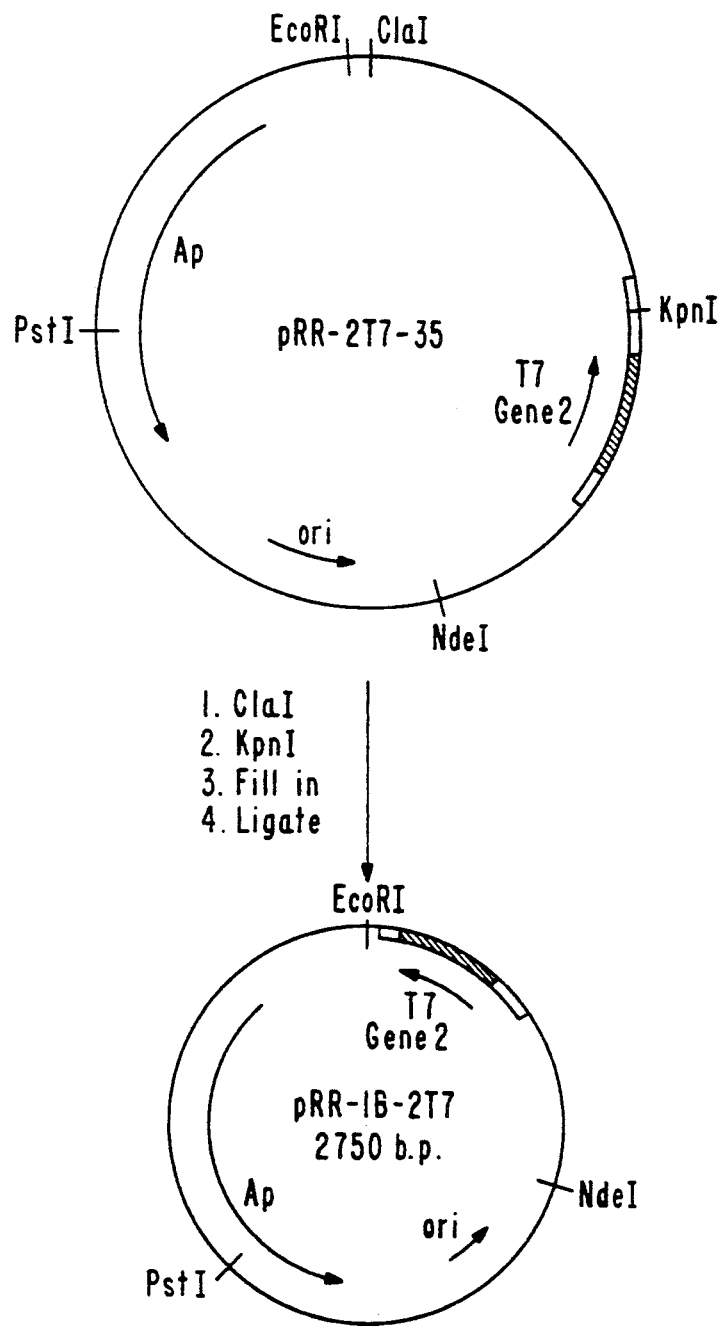

FIG. 7 shows how pRR-2T7-35 was reduced in size by cleaving out the ClaI/KpnI fragment forming pRR-1B-2T7.

Figure 8:
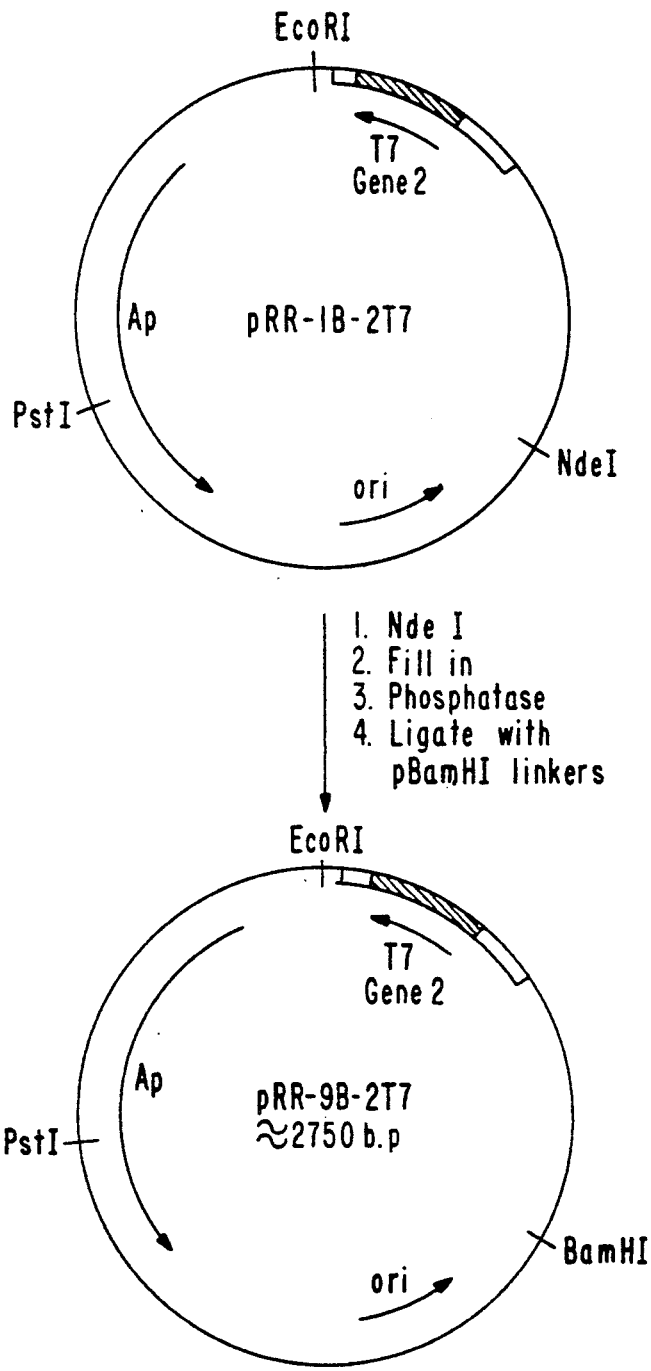

FIG. 8 shows how the NdeI site of pRR-1B-2T7 was changed to a BamHI site.

Figure 9:
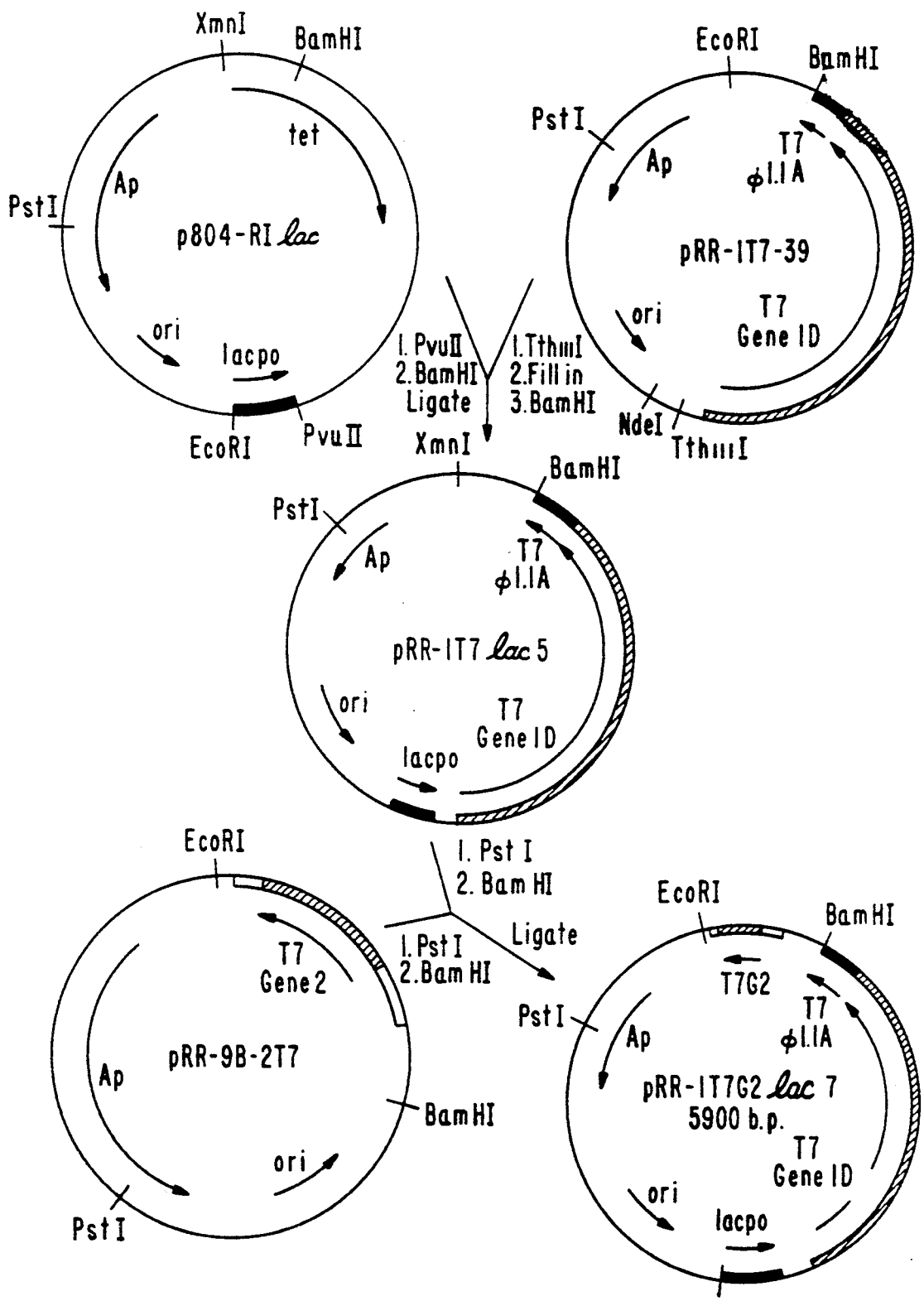

FIG. 9 schematically shows the procedure used to clone T7 Gene 2 in tandem with the T7 Gene 1D. T7 Gene ID was cloned again into the PvuII region of p804-RI lac, with the ligation forming pRR-1T7 lac 5. The only difference between pRR-1T7 lac 5 and p1T7L-3 (FIG. 5) is that pRR-1T7 lac 5 has an XmnI restriction site where p1T7L-3 has an Eco RI site. T7 Gene 2 was cloned into pRR-1T7 lac 5 as a PstI/BamHI fragment forming pRR-1T7G2 lac 7. This T7 Genes 1D and 2 arrangement is an Eco RI restriction fragment.

Figure 10:
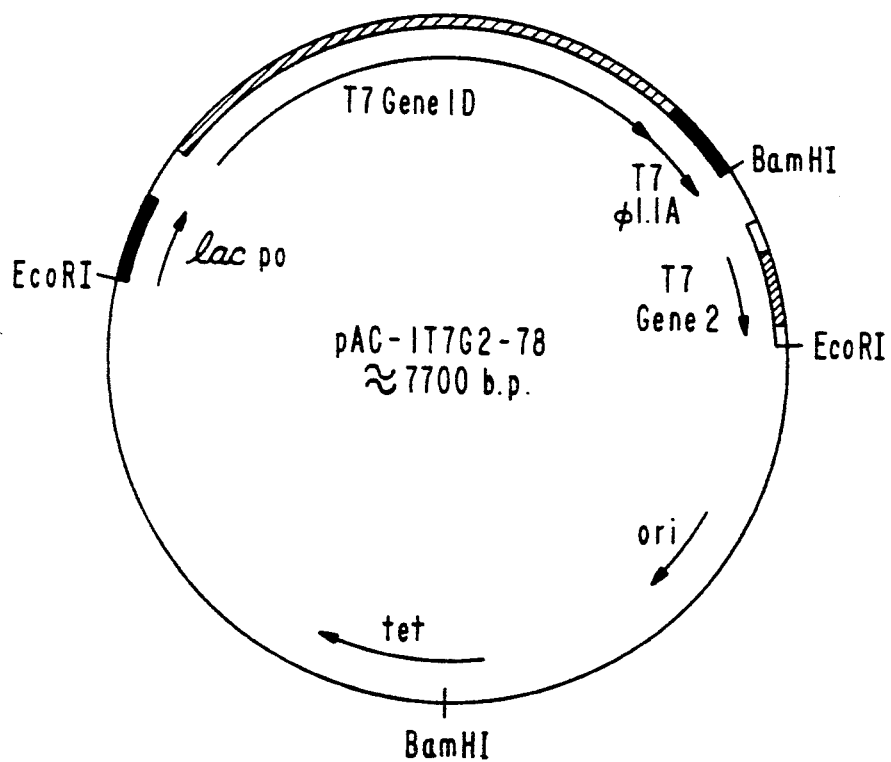

FIG. 10 shows the structure of pAC-1T7G2-78. It was constructed by cloning the T7 Genes 1D and 2 Eco RI restriction fragment from pRR-1T7G2 lac 7 into the Eco RI restriction site of pACYC 184.

Figure 11:
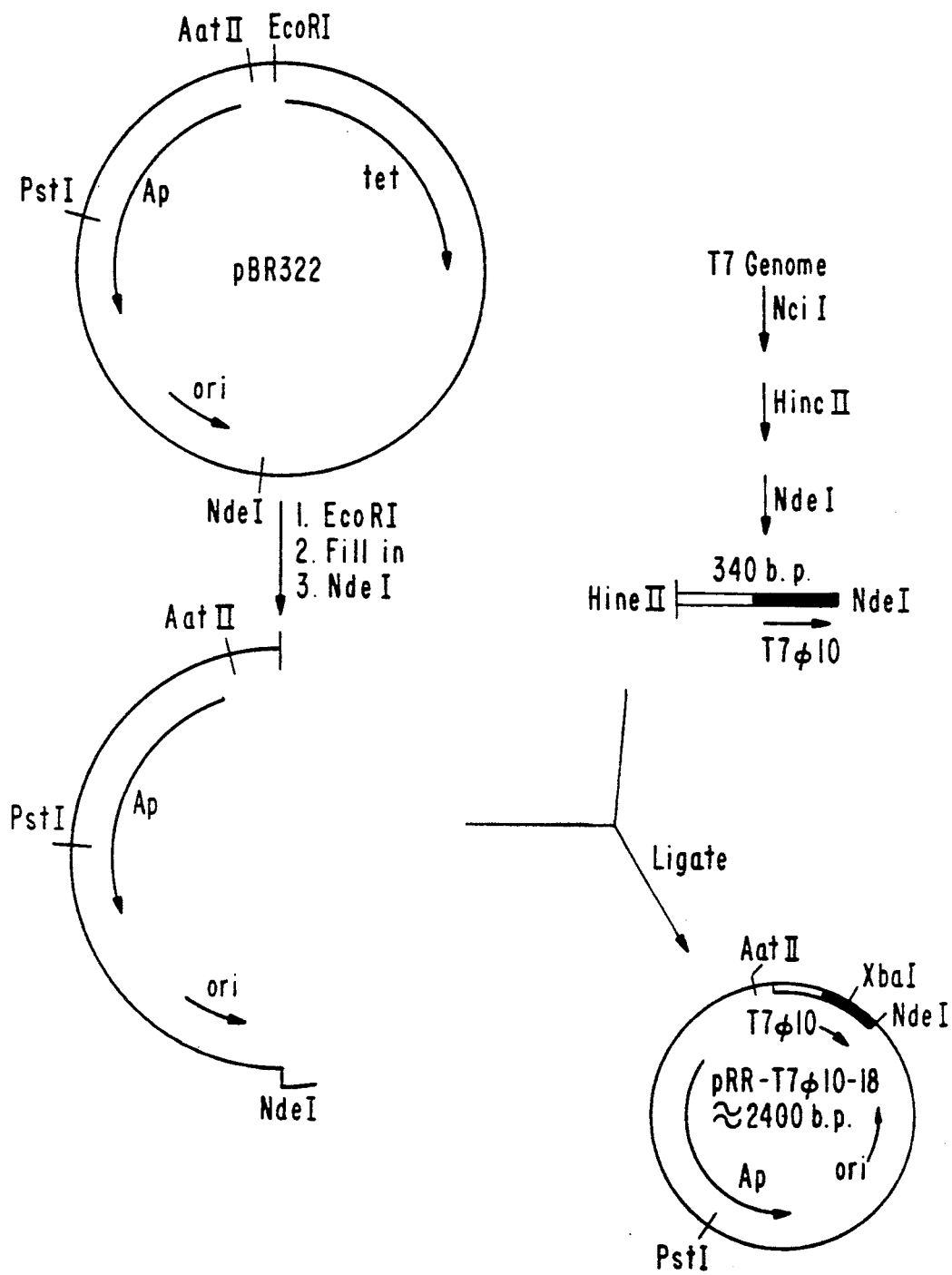

FIG. 11 shows the steps employed to clone the T7 Gene 10 promoter, recreating the NdeI restriction site. Starting with the T7 genomic DNA a series of restriction enzyme digestions were made to obtain the 340 base pair fragment containing the T7 Gene 10 promoter. This was cloned with a fragment derived from pBR322. The plasmid isolated, pRR-T7$\phi$10-18 can be opened at the NdeI site so that any gene can be cloned into a position allowing the T7 promoter to direct its expression in the presence of mutant T7 RNA polymerase.

Figure 12:
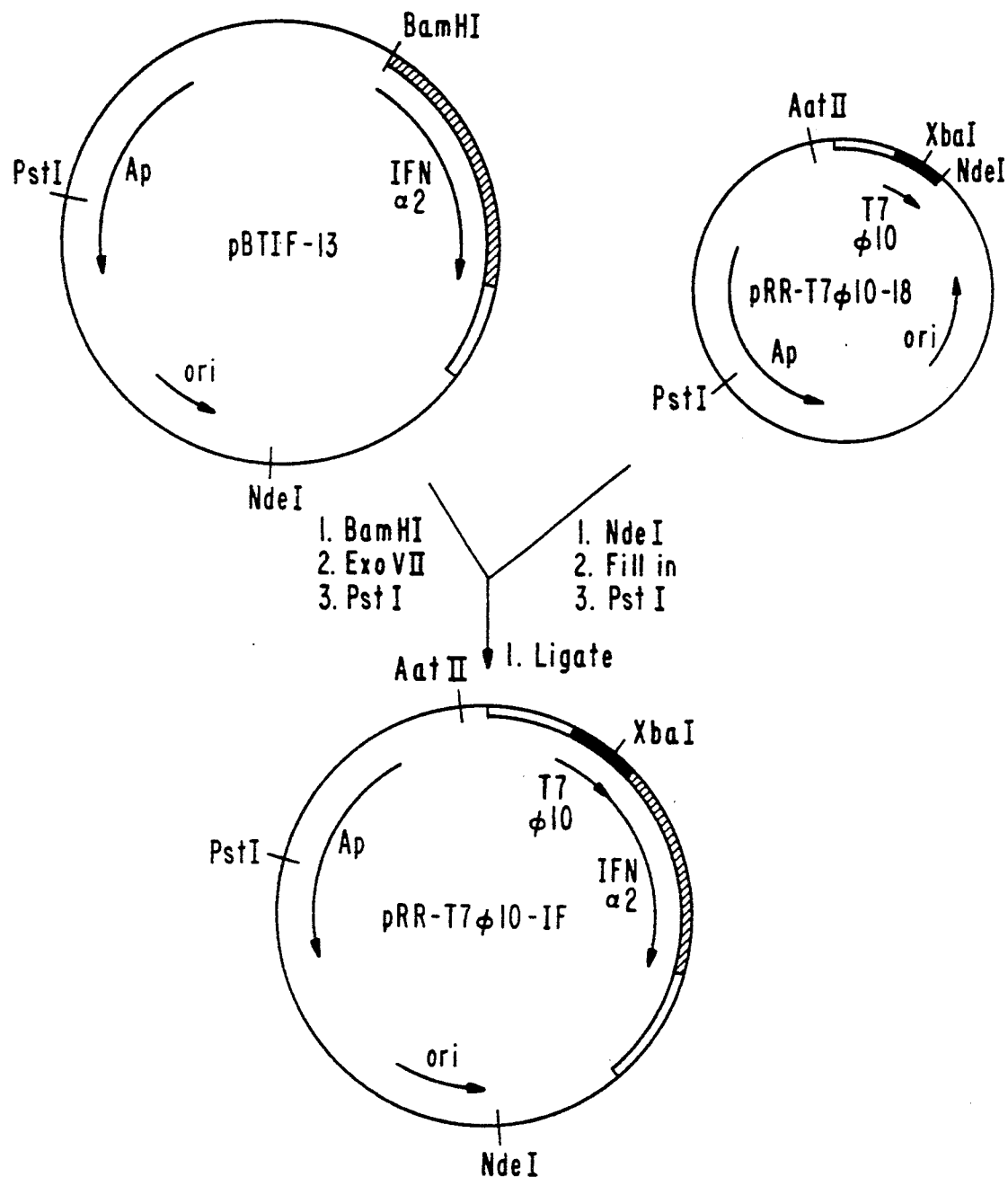

FIG. 12 schematically depicts how the T7 Gene 10 promoter was cloned proximal to the alpha-2 interferon gene. The plasmid construction shown, pRR-T7$\phi$10-IF, has the alpha-2 interferon gene in a position to allow its expression by mutant T7 RNA polymerase under the control of the T7 Gene 10 promoter.

Figure 13:
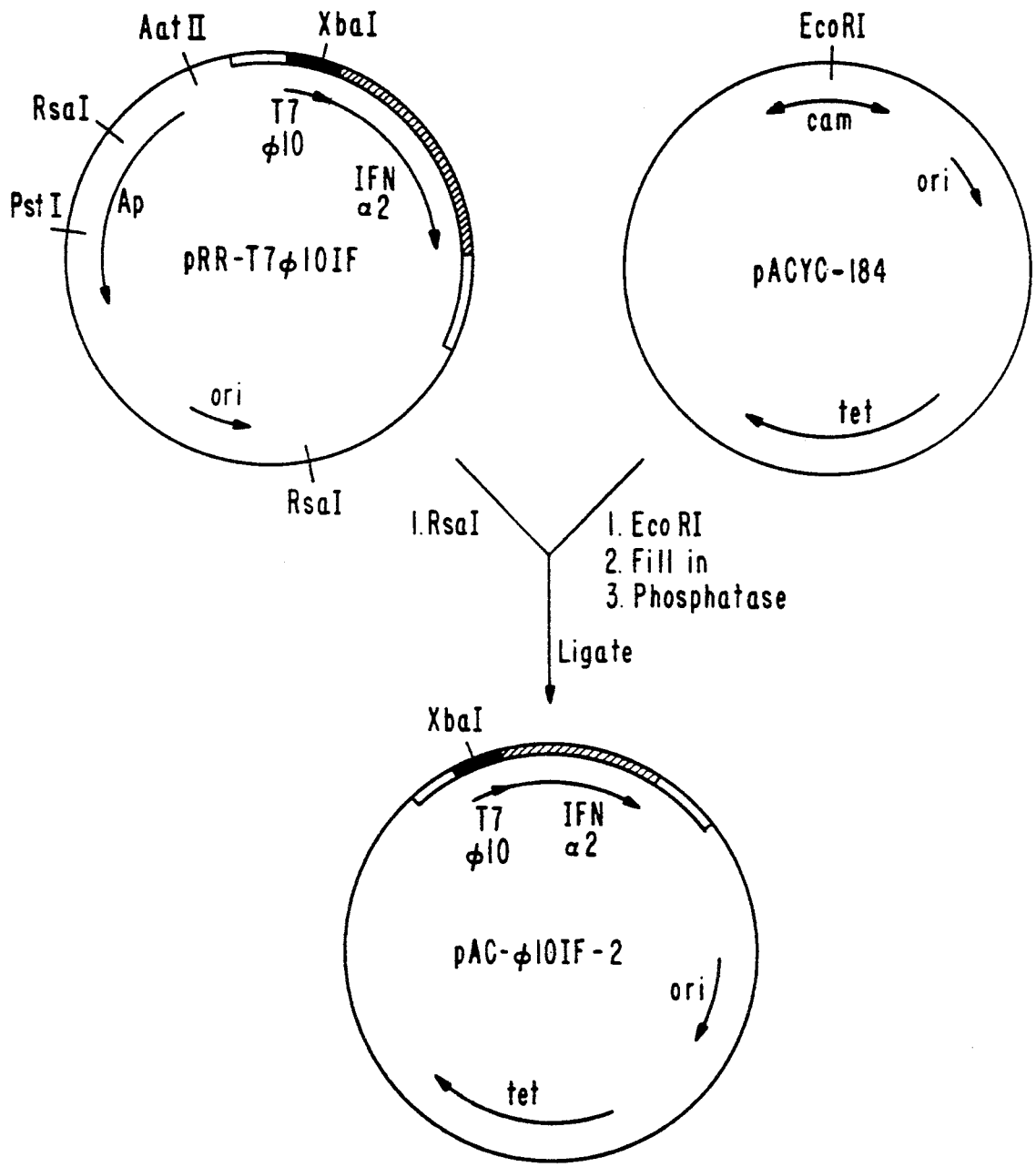

FIG. 13 shows schematically how pRR-T7$\phi$10-IF was digested with RsaI and cloned into pACYC 184 as a blunt end fragment. pAC-$\phi$10IF-2 consists of a T7 promoter heterologous gene complex in a pACYC184 vehicle which is compatible with pBR322 in the same cell.

Figure 14:
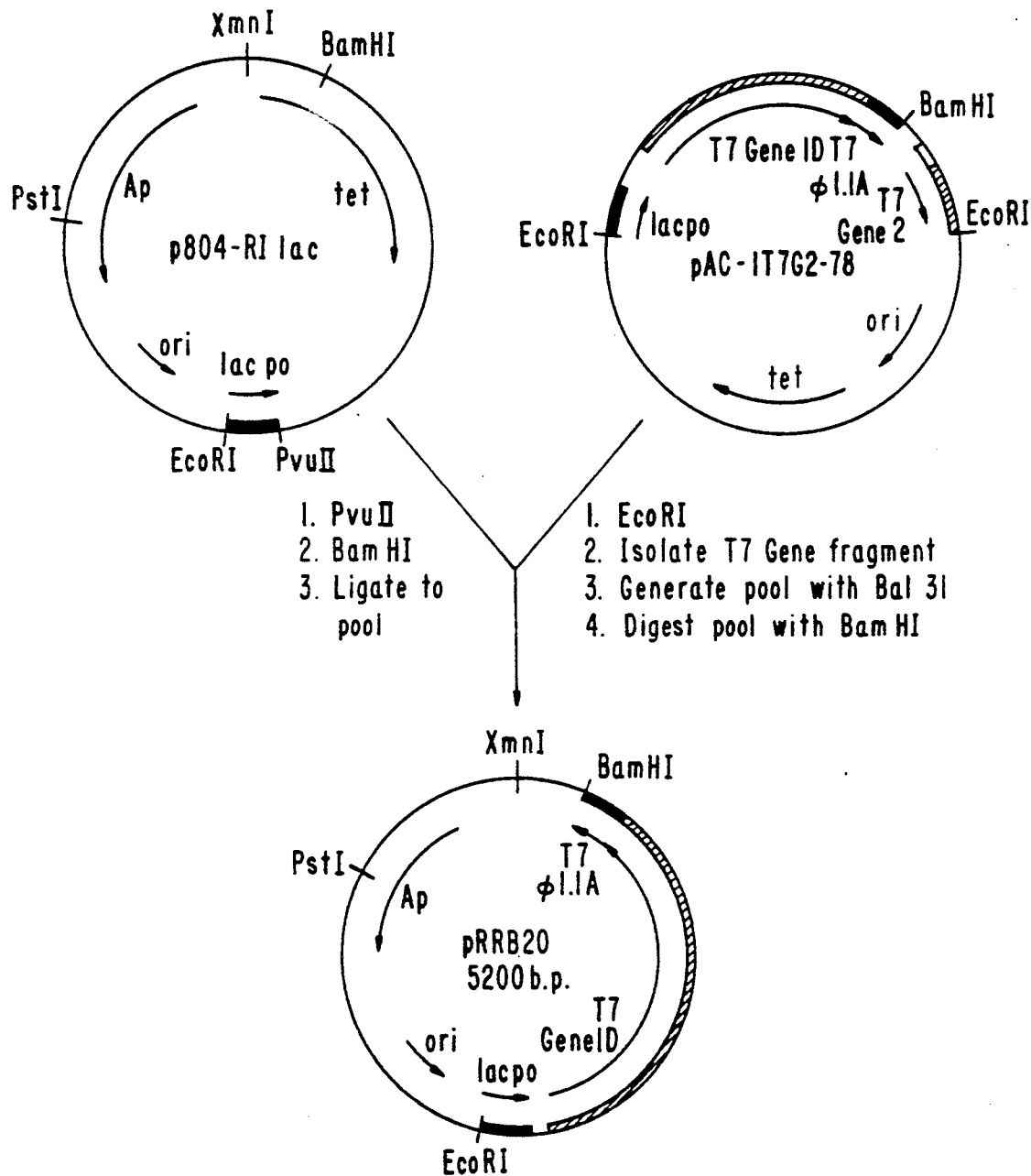

FIG. 14 shows how a variety of clones were generated by digesting the T7 gene Eco RI fragment of pAC-1T7G2-78 with Bal 31. The enzyme was allowed to digest through the lac promoter region into the pBR322 DNA intervening between the promoter and the start of the T7 Gene 1D coding region. A pool of variable length fragments was then created by digestion with BamHI. These fragments were cloned adjacent to an intact lac promoter by digesting p804-RI lac with PvuII/BamHI. A variety of clones were isolated. One of them, pRRB20, was used in the two plasmid system and is shown in the FIG. 14.

Figure 15:
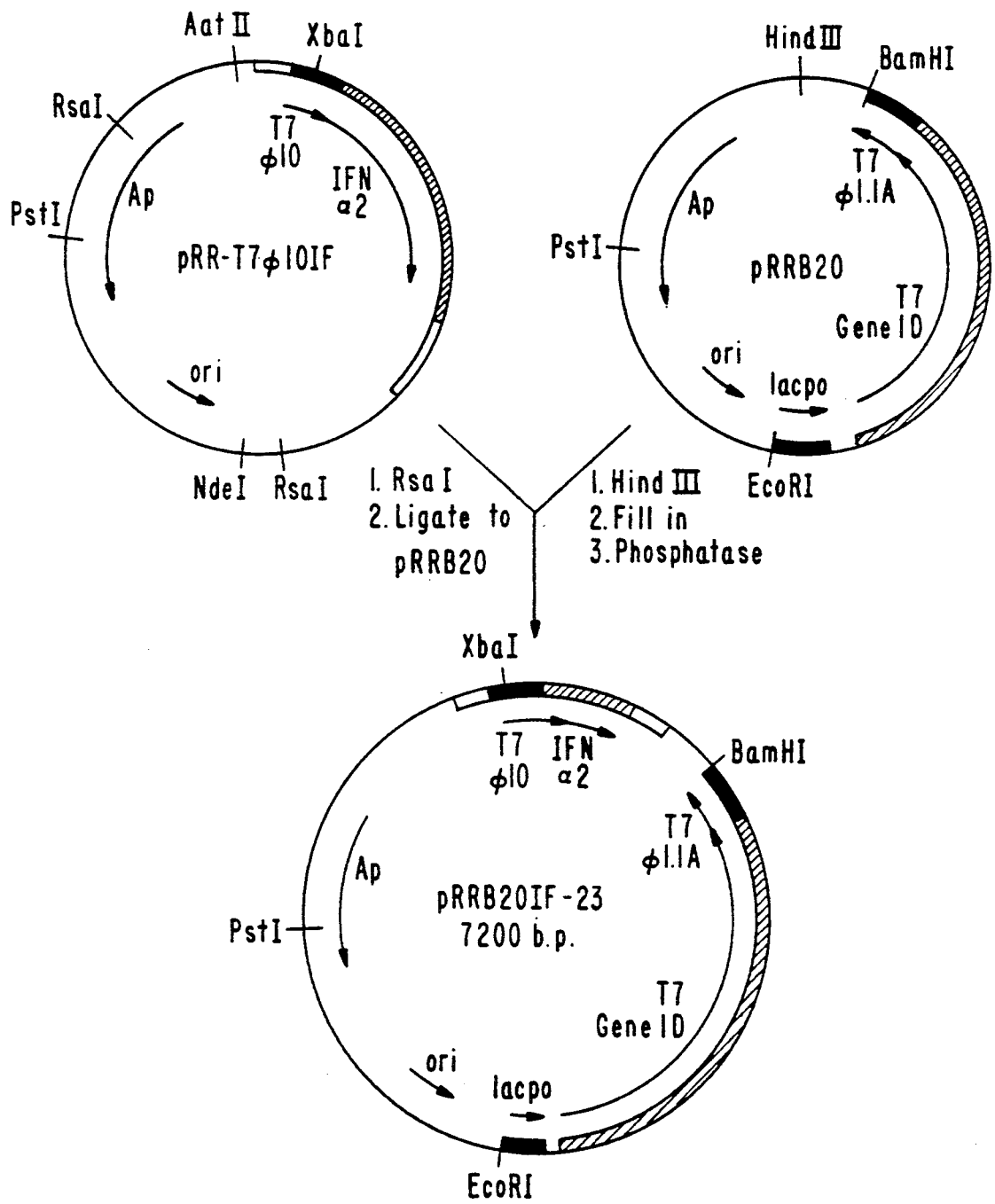

FIG. 15 shows schematically the one plasmid system. A blunt end, RsaI fragment containing the T7 Gene 10 promoter - alpha 2 interferon complex was cloned into the Hind III site of pRRB20 which had been blunt ended. pRRB20IF-23 was isolated and the particular orientations of the genes and promoters involved in the T7 one plasmid system is illustrated.

FIG. 16 shows the nucleotide sequence of DNA encoding the amino-terminal portion of bacteriophage T7 RNA polymerase.

DESCRIPTION OF THE INVENTION

All references cited herein are hereby incorporated in their entirety by reference. Whenever the word "polypeptide" or "protein" is used below, it will be understood that both polypeptides and proteins are intended.

Bacteriophage T7 DNA can be extracted from wild-type phage T7, which can be obtained from commercial sources including the American Type Culture Collection (ATCC No. 11303-B7). The method of isolating the purified bacteriophage DNA is essentially that described in Maniatis et al., supra, pp. 76-85. The DNA so obtained can be cut with various restriction endonucleases to yield the desired T7 bacteriophage promoters and structural gene fragments (e.g., as described below.) The complete bacteriophage T7 DNA sequence is known [Dunn et al., J. Mol. Biol. 166:477 (1983)]. The nomenclature utilized herein is described in this publication.

The T7 promoters are known to vary in strength and have been assigned to 3 classes on this basis. The strongest of these are the Class III promoters, which is the class of promoters preferred for use in this invention. One of the Class III promoters that regulates the expression of gene 10 protein (T7 $\phi$10) has been utilized to illustrate the invention. Due to the nature of the restriction sites conveniently located in bacteriophage T7 DNA, the bacteriophage T7 RNA polymerase gene exemplified below was always accompanied by another intact T7 promoter region. This promoter region (T7 $\phi$1.1A), which is present in the exemplary constructs in addition to the T7 promoter region utilized to initiate transcription of the gene for the desired polypeptide, is unnecessary and can be deleted if desired. As explained above, this construction had been predicted by the art [Proc. Natl. Acad. Sci. USA 81:2035 (1984)] to result in an autocatalytic increase both in the level of T7 RNA polymerase and in the rate of transcription of the plasmid which would lead to the death of the cell. Surprisingly, this morbidity does not occur with the mutant polymerases used in the present invention.

There are two principal systems, through the use of which the expression of a gene which codes for a desired polypeptide may be placed under the control of a bacteriophage T7 promoter region. These systems are the "dual plasmid system" and the "single plasmid system".

Such systems are capable of working within any host background such as bacterial, yeast, mammalian or plant backgrounds, as long as transcription of the T7 RNA polymerase is under the control of a regulatable host-specified promoter and the nucleotide sequence coding for the heterologous protein is under the control of a T7 promoter sequence.

Dual Plasmid System

To produce this system, two vectors are selected which will be compatible in the chosen host. These vectors should contain conveniently located restriction sites and appropriate drug selection markers as are customarily and ordinarily used in recombinant DNA research experiments. Vector compatibility, i.e., the ability of two vectors to co-exist in the same host cell depends on the process of replication and partitioning employed by each of the vectors. Plasmids that share at least one common step in either of these processes would compete for maintenance, thereby leading to plasmid incompatibility. It is known that pBR322, a Col El derivative, is compatible with pACYC 184 [Chang et al., J. Bact. 134:1141 (1978)].

As a first step toward the construction of a representative dual plasmid system, the lac UV5 promoter was cloned into pBR322 so that a unique restriction site could be used to place a desired gene directly under the control of the lac UV5 promoter. T7 Gene ID (described below) was cloned distal to the lac UV5 promoter at this restriction site, thereby facilitating the synthesis of mutant T7 RNA polymerase on induction of the lac UV5 promoter by IPTG. The lac UV5 promoter constitutes two mutations in the RNA polymerase interaction site, which make it independent of CAP-cAMP regulation. The mutations have an enhancing effect on the RNA polymerase-DNA open complex formation; thereby leading to increased transcription initiation. This property makes it a much stronger promoter than the wild type lac promoter. Since it was believed that T7 Gene 1 was potentially lethal when expressed, it was believed that its expression had to be tightly controlled until needed and/or a less potent mutant form of the polymerase had to be utilized. Therefore, the plasmid was transformed and maintained in a host strain comprising a chromosomally located lac I$^q$ repressor. This strain produces about 10 times more lac repressor molecules when compared to the wild type lac I+ strain. E. coli RB791 is a lac I$^q$ strain which has been deposited with the American Type Culture Collection under accession No. 53622.

The I$^q$ background should be suitably functional both as a plasmid-borne characteristic (Davanloo, P. et al., supra) or when chromosomally located. In practice, any desired E. coli strain can be made amenable to this system by introducing into it a functional I$^q$ gene on a plasmid. Theoretically, an I$^q$ background may not be mandatory in the case where this system is present in a single or low copy format. Such a system could be effectively controlled by manipulating both the promoter strength and the gene copy number, such that the repressor molecules provided by the lac I+ background are sufficient to repress the T7 Gene 1Dsynthesis effectively until induced.

Control of T7 Gene 1D expression in E. coli is not limited to a repressed lac po system. Various regulatory elements may be used to regulate its expression given an appropriate E. coli host background. For example, the bacteriophage lambda $P_L$ system may be used in which the promoter is controlled by a temperature sensitive repressor (e.g., CI 857). T7 Gene 1D expression thus regulated can be induced by raising the temperature.

In the example below, a DNA fragment bearing the T7 $\phi$10 promoter was isolated by a series of restriction enzyme reactions and cloned into a pBR322 vehicle so that a convenient restriction site was reformed to enable insertion of a gene coding for any desired polypeptide. Once the gene for the desired protein had been inserted and characterized, the T7 promoter/desired gene complex was transferred to a plasmid vector compatible with a pBR322 based vector. These cells, when induced with IPTG, produced the desired protein.

The mutant T7 polymerases of the present invention are encoded by DNAs having the sequence described by Dunn et al., J. Mol. Biol. 166:477 (1983), except that the DNAs have been severely truncated by genetic change. In the example below, there is a single base deletion at a position corresponding to wild-type T7 base 3809. The resulting frame shift causes polypeptide chain termination at T7 base 3877 and produces an enzyme having only about 25% of the amino-terminal amino acid residues of the wild-type enzyme. Similar results can be produced by DNA encoding T7 polymerase in which there is a base deletion(s) occurring anywhere between the bases corresponding to bases 3809 and 3877 of a wild-type T7 RNA polymerase gene which produces a similar frame shift. Alternatively bases beyond about base 3809 can simply be entirely deleted without use of a frame-shift mutation.

The relevant regions of the sequence described in the publication of Dunn et al., supra, are shown in FIG. 16, wherein bases 1 and 709 correspond to bases 3171 and 3879, respectively, in the publication. Base 639 in FIG. 16 (shown underlined) corresponds to base 3809 in the publication.

The DNA coding for a T7 deleted gene in the example below is referred to herein as T7 gene 1D and the gene product is referred to as the mutant T7 RNA polymerase. T7 Gene 1D and other mutant genes can be obtained in a number of ways known to those skilled in the art. Chemical synthesis and chemical deletion of a base(s) in isolated Gene 1 are two methods that are well established in the art. Primer-directed site-specific mutagenesis described by Morinaga et al., Bio/Technology 2:636 (1984) can also be used.

Mutations in the intact gene for T7 polymerase can also be made using known mutagenic agents. Such mutants can be screened for the precise location of the base deletion(s) prior to being used for plasmid construction using standard DNA sequencing techniques [see, e.g., Sanger et al., Proc. Natl. Acad. Sci. USA 74:5463 (1977) and Tabor et al., Proc. Natl. Acad. Sci. USA 84:4767 (1987)].

Single Plasmid System

To illustrate this embodiment of the invention, a plasmid containing the lac UV5 promoter/T7 Gene complex (pRRB20) was cut at a unique restriction site and blunt-ended, and the fragment containing the phage T7 promoter/desired gene complex (obtained from a pBR322-based clone described below) was then ligated into the cleavage site. This resulted in a single pBR322-based plasmid that carried all the necessary functional entities for the T7 expression system. These plasmids, when transformed into a lac I$^q$ containing host, enabled the isolation of stable clones which, upon induction with IPTG, were found to produce large quantities of the desired protein.

In this single plasmid system, plasmids which comprise the T7 φ10/desired gene complex oriented both in the same and opposite transcriptional direction as the lac UV5 promoter/T7 Gene 1D complex were constructed. Strains harboring both plasmid types were viable and functional.

Host bacterial cells producing heterologous proteins according to the methods of this invention can be identified and/or prepared for protein isolation using standard methods. Generally, it is necessary to first disrupt the cells. This can be accomplished by sonication or by other mechanically disruptive means such as a French pressure cell or Gaulin homogenizer.

Cell disruption can also be accomplished by chemical or enzymatic means. Since divalent cations are often required for cell membrane integrity, treatment with appropriate chelating agents such as EDTA or EGTA might prove sufficiently disruptive to facilitate the leakage of the proteins from the cells. Detergents such as sodium dodecylsulfate (SDS) and chaotropic agents such as guanidine-hydrochloride can also be used to disrupt the cells. Similarly, enzymes such as lysozyme have been used to achieve the same result. That enzyme hydrolyzes the peptidoglycan backbone of the cell wall.

The application of osmotic shock can also be employed. Briefly, this can be accomplished by first placing the cells in a hypertonic solution which causes them to lose water and shrink. Subsequent placement in a hypotonic "shock" solution leads to a rapid influx of water into the cells, with an expulsion of the desired proteins.

Once freed from the cells, the proteins can be identified using known methods. For example, a bioassay based upon the use of cells responsive to a biological activity of the proteins can be used, or a radioimmunoassay or enzyme-linked immunosorbent assay can be carried out using antibodies against the proteins. Polyacrylamide gel electrophoresis followed by Western blotting or similar analysis can be used for rapid screening.

The proteins can be concentrated by precipitation with salts such as sodium or ammonium sulfate, ultrafiltration or other methods well known to those skilled in the art. Further purification can be accomplished by conventional protein purification techniques including but not limited to gel filtration, ion-exchange chromatography, preparative disc-gel or curtain electrophoresis, high performance liquid chromatography (HPLC), isoelectric focusing, low temperature organic solvent fractionation or countercurrent distribution.

EXAMPLE

Unless otherwise specified, percentages given below for solids in solid mixtures, liquids in liquids, and solids in liquids are on a wt/wt, vol/vol and wt/vol basis, respectively.

Bacterial Strains

*E. coli* 294, a K12 derivative, was used as a host for all clonings except when T7 genes were placed under lac promoter control and in DNA sequence analyses experiments. The genotype of *E. coli* 294 (end A−, hsd R−, thi−, pro−) has been described by Bolivar et al. [Methods in Enzymology 68:245 (1979)] *E. coli* D1210 (a derivative of *E. coli* HB101) was used as a host in cloning where T7 genes were placed under lac control. This strain has been described by Sadler et al. [Gene 8:279 (1980)] and contains chromosomally located lac I$^q$ and Y+ genes. *E. coli* RB791 was obtained from the *E. coli* Genetic Stock Center, Yale University School of Medicine, New Haven, Conn. Its genotype is lac I p4000 (lac I$^q$), lac Z p4008 (lac L8), λ−, IN(rrn D - rrn E) 1, [Brent et al., Proc. Natl. Acad. Sci. USA 78:4204 (1981)]. *E. coli* JM103 was used for cloning with M13 to sequence the intervening region between the lac promoter fragment and T7 Gene 1. This organism is available from the American Type Culture Collection (ATCC 39403). Its genotype is Δ (lac, pro), thi−, str A, end A, sbc B15, hsd R− sup E,F' tra D36 pro A+, pro B+, lac I$^q$, lac Z M15.

Growth Medium

A 20-10-5 TYE broth and agar medium was used throughout (20 g Bacto-Tryptone, 10 g Bacto Yeast Extract, 5 g NaCl per liter H$_2$O) and was supplemented with appropriate antibiotics needed for selection (ampicillin, 75 ug/ml or tetracycline HCl, 20 ug/ml). Both antibiotics were purchased from Sigma Chemical Co., St. Louis, Mo.

Preparation of T7 Phage DNA

Wild type T7 bacteriophage was obtained and the T7 DNA was isolated and purified essentially by the methods described by Maniatis et al., supra, for bacteriophage lambda, except that the T7 bacteriophage were spun at 30K rpm overnight in a 70.1 Ti rotor. The concentration of CsCl was 0.81 g per 1 ml of phage suspension.

Plasmid Vectors and Other Genetic Elements

Two cloning vehicles were used; pBR322 [Sutcliffe, Nucleic Acids Res. 5:2721 (1978)] and pACYC 184 [Chang et al., J. Bacteriol. 134:1141 (1978)]. The lac promoter (lac po) was originally described by Backman et al., [Proc. Natl. Acad. Sci. USA 73:4174 (1976)] and was originally derived from pKB252. The amino terminal portion of T7 Gene 1 was isolated from pT7-13 [Stahl et al., J. Mol. Biol. 24:481 (1981)], which was a gift from S. Stahl.

Testing of RRB Strains for Production of Alpha-2 Interferon in the Two Plasmid System

*E. coli* D1210 recombinants that contained the human alpha-2 interferon encoding nucleotide sequences under T7 promoter control were tested for human alpha-2 interferon synthesis in the following manner. The recombinant organisms were streaked on 20-10-5 agar plates containing 100 ug/ml ampicillin and 20 ug/ml tetracycline HCl and incubated overnight at 30° C. In the morning, a 5 ml suspension of cells in 20-10-5 broth was made from a plate scraping. The cell suspension was immediately diluted into 50 ml of 20-10-5 containing 30 ug/ml ampicillin and 20 ug/ml tetracycline in a 250 ml Erlenmeyer flask. The flasks were shaken at 250 rpm in a New Brunswick microtherm water bath shaker at 37° C. The cell turbidity was monitored with a Klett-Sommerson colorimeter at wavelength 500 (green filter) and when the density reached approximately Klett 200 the zero time sample was taken. At this time, IPTG was added to a final concentration of 5mM. A parallel control experiment was performed in which IPTG was not added to the culture. Triplicate 1 ml samples were taken every hour from both flasks for interferon assay and cell density.

The single plasmid system was tested for alpha-2 interferon production as follows: *E. coli* D1210 and *E.* coli RB791 were separately transformed with the pRRB20IF23 construction and were separately tested for alpha-2 interferon production upon induction with IPTG. Cells were grown overnight on 20-10-5 agar plates containing 100 ug/ml ampicillin. After about 18 hours of growth, a 5 ml suspension of cells made from a plate scraping was diluted into 500 ml of fresh 20-10-5 broth containing 75 ug/ml ampicillin and was shaken at 300 rpm, at 30° C. on a New Brunswick G-52 rotary shaker until a Klett O.D. of 200 was reached. At this time, 50 ml aliquots were transferred to 250 ml Erlenmeyer flasks and placed at 37° C. in a New Brunswick microtherm water bath shaker. Zero time samples were taken and 5mM IPTG was added to the appropriate flasks. The flasks were shaken at 250 rpm and triplicate 1 ml samples were taken every two hours up to six hours post induction, and then once again after continuous overnight incubation (about 20 hours post induction).

Interferon Assay Procedure

One ml of culture was pipetted to a 1.5 ml eppendorf tube, and the sample was centrifuged for 1 minute in a Brinkman microfuge. The supernatant was poured off and the pelleted cells were resuspended in 0.2 ml of lysing buffer (50 mM Hepes, 30 mM NaCl, 1% SDS, 1% β-Mercaptoethanol, 5M Urea; pH 7.0). The suspension was heated for 1 minute at 90° C. and then diluted with cold phosphate buffered saline (PBS) to the original volume. The samples were vortexed and centrifuged in a Brinkman microfuge for 1 minute. 0.1 ml aliquots were withdrawn for a dilution and subsequent assay.

Alpha-2 interferon protein is characterized as having an antiviral activity of at least $1 \times 10^7$ units/mg as determined by the cytopathic effect-inhibition assay employing EMC virus and human foreskin cells (FS-71) performed essentially as described by Familletti et al., [Methods in Enzymology 78:387 (1981)], using the NIH/WHO natural leukocyte interferon standard 69/19 as a standard.

Enzymes and Enzyme Reactions

All enzymes and linkers, except for Exo VII, were obtained from New England Biolabs, Inc., Beverly, Mass. Exo VII enzyme was obtained from Bethesda Research Laboratories, Inc., Rockville, Maryland. The reactions were carried out essentially according to the specifications in the manufacturers, catalogs.

Electrophoresis and DNA Isolation Techniques

Agarose gel electrophoresis and polyacrylamide gel electrophoresis techniques were carried out essentially as described by Maniatis et al., supra. Isolation and recovery of DNA fragments from agarose or polyacrylamide gels were performed essentially as described by Smith [Methods in Enzymology 65:371 (1980)].

Large and Small Scale (mini) Preparation of Plasmids

The preparation technique used herein for the large scale isolation of plasmids was the alkaline-SDS lysis method essentially as described by Maniatis, et al., supra. Large numbers of clones were also screened essentially by the alkaline-SDS lysis method described by Maniatis et al., supra, except that the cells employed were generally obtained from a 10 ml overnight culture.

Transformation Procedure

The method for transforming E. coli was performed essentially as described by Dagert et al., Gene 6:23 (1979).

DNA Sequencing

The sequence of the promoter region of pRRB20 was determined by the M13 cloning and DNA sequencing system of New England Biolabs, Beverly Mass., which uses the cloning vectors developed by Messing et al. [Gene 19:269 (1982)] and the sequencing techniques of Sanger et al. [Proc. Natl. Acad. Sci. USA 74:5463 (1977)].

The sequence of the T7 RNA polymerase DNA was determined by the double stranded "Sequenase" variation of the Sanger method. This technique was developed by Tabor et al. [Proc. Natl. Acad. Sci. USA 84:4767 (1987)]. The Sequenase kit was purchased from United States Biochemical Corp., Cleveland, Ohio. A series of oligonucleotide primers were synthesized using an Applied Biosystems, 380A DNA synthesizer. All chemicals for synthesis were purchased from Applied Biosystems, except for acetonitrile which was purchased from J. T. Baker Inc., Phillipsburg, N.J.

T7 and pBR322 Genome Locations

Locations given for restriction enzyme sites and for promoters and genes on the T7 genome were determined from the sequence published by Dunn et al., supra. Locations are defined by base pair (b.p.) number according to the convention of the above authors. Locations for restriction enzyme sites and base pair numbers in pBR322 are defined by the sequence described by Maniatis et al., supra.

Cloning of T7 Gene 1 (T7 RNA polymerase)

The T7 RNA polymerase gene begins at b.p. 3171 and ends at b.p. 5820 of the T7 genome. The entire gene was assembled from two fragments cloned separately. The carboxy terminal end of the gene was cloned directly from T7 genomic DNA, as follows: The T7 genome was digested with Mbo I, and an 8311 b.p. fragment was isolated by agarose gel electrophoresis. This fragment was subsequently digested with Nci I. Nci I sites at b.p. 2660 and b.p. 7589 yielded a 4929 b.p. fragment which was isolated by agarose gel electrophoresis. This fragment was then further digested with Hae III. A 1136 b.p. fragment, representing the T7 genome from b.p. 4744 to b.p. 5880 and encompassing the T7 RNA polymerase 1.1A promoter, was isolated by agarose gel electrophoresis.

Construction of pRR19: pBR322 was digested with Bam HI, and the site was filled in with DNA polymerase I large fragment (Klenow fragment). The blunt ended 1136 b.p. T7 fragment was then ligated into the Bam HI digested/filled in blunt-ended fragment derived from the plasmid pBR322 and the ligated fragments were transformed into E. coli 294. The combination of the filled in Bam HI site and the Hae III site recreates a Bam HI site, which was used as a marker to screen clones for the presence of the 1136 b.p. fragment. pRR19 was isolated in this way (FIG. 1). The orientation was deduced by observing the distance of the assymetrically placed Hpa I site present in the proximal end of the 1136 b.p. fragment with respect to the nearby Hae III sites of the pBR322 plasmid.

Construction of pRR-1T7-39: The amino terminal coding sequence of T7 Gene 1 was obtained from pT7-13 and was joined to its carboxy terminal coding sequence contained in pRR19 by taking advantage of the Kpn I site common to both fragments. This site is located in the T7 genome at b.p. 5614.

pRR19 was digested with Kpn I and Pvu II. The large fragment containing the origin of replication and ampicillin resistance gene was isolated by agarose gel electrophoresis. pT7-13 was digested with Pst I, blunt-ended using the Klenow enzyme and then cut with Kpn I. The Gene 1 containing fragment was isolated by agarose gel electrophoresis and ligated to the pRR19 vehicle prepared above. The ligated fragments were transformed into E. coli 294. Clones were screened by digesting the plasmid DNA with Kpn I and Hpa I. The plasmid pRR-1T7-39 (FIG. 2) was isolated from this screen. The T7 DNA contained in this plasmid extends from b.p. 3117 to b.p. 5880 of the T7 genome.

The T7 DNA encoded in pRR-T7-39 was sequenced and found to have a single base deletion at T7 base 3809. The resultant frame shift caused a polypeptide chain termination at position 3877. This resulted in a polypeptide chain consisting of approximately 27% of the amino terminal end. This clone was used in all subsequent constructions and is referred to as "T7 Gene 1D". The gene product is referred to herein as the mutant T7 RNA polymerase.

The lac Promoter (lac po) System

The lac po sequence used was a UV5 derivative. The original promoter fragment existed as a 203 b.p. Hae III fragment. The sequence used in this construction consisted of a 125 b.p. fragment bracketed by Eco RI and Pvu II sites. It was constructed by digesting pKB252 with Eco RI and separating the fragments in a 10–40% glycerol gradient, which was run for 24 hours at 24K rpm in an SW 27 rotor. The small fragment was collected by pooling several gradients and was then digested with Alu I. pBR322 was digested with Eco RI and Pvu II and the large fragment containing the origin of replication and the ampicillin resistance gene was isolated by agarose gel electrophoresis. The recovered pBR322 DNA was then ligated to the Alu I digested small DNA fragment and the ligated mixture was transformed into E. coli 294 and plated on 20-10-5 agar plates containing ampicillin and 5-bromo-4-chloro-3-indolyl-β-D-galactoside. One of the screened clones had a 125 b.p. fragment. The nucleotide sequence of this fragment was determined to be:

GAATTCCAGTGAATCCGTAATCATGGTCATAGCTCACTCATTAGGCACCCCGGC-

TTTACACTTTATGCTTCCGGCTCGTATAATGTGTGGAATTGTGAGCGGTAACAA-

TTTCACACAGGAAACAG

The 125 b.p. fragment was cloned into the Eco RI/Pvu II region of P804-RI which was constructed from pBR322 (FIG. 3). In this scheme, the original pBR322 Eco RI site was filled in and religated (creating an Xmn I site), and Eco RI linkers were inserted into the filled-in Nde I site. After insertion of the lac 125 b.p. po fragment, the resultant plasmid was designated P804-RI lac (FIG. 3, bottom).

Cloning T7 Gene 1D Under lac po Control pRR-1T7-39 was digested with Tth111 I, the digested site was filled in, and the plasmid was then digested with Pst I. The T7 gene fragment was isolated by agarose gel electrophoresis. p804-RI lac was digested with Pvu II and Pst I. The fragment containing the lac po and the origin of replication was isolated by agarose gel electrophoresis and ligated to the isolated pRR-1T7-39 T7 Gene 1D fragment. The DNA was transformed into E. coli D1210. From the screened clones, pRR-1T7L-3 was isolated (FIG. 4, bottom).

E. coli D1210 cells carrying pRR-1T7L-3 did not grow on 20-10-5 agar in the presence of isopropyl-β-D-thiogalactoside (IPTG) suggesting that T7 Gene 1D product was inhibitory to E. coli cells. This was tested in an experiment in which IPTG was added to broth cultures containing cells harboring T7 Gene 1D under lac po control. When cells growing in the log phase at 37° were induced with IPTG, there was a gradual cessation of growth followed by a death phase. The onset of the death phase is even more pronounced at 42° C. IPTG (2 mM) containing agar plates were subsequently used to initially screen for any recombinant constructions in which T7 Gene 1D was under the lac po control.

Cloning of T7 Gene 2

T7 Gene 2 is located from b.p. 8898 to b.p. 9090 of the T7 genome. The protein's function is to inactivate the hose RNA polymerase. The largest Hae III fragment of the T7 genome extending from b.p. 7579 to b.p. 10309 encompasses T7 Gene 2. The Hae III fragment was isolated by agarose gel electrophoresis. The isolated DNA was then further digested with Hinc II. The Hinc II restriction sites at b.p. 8765 and b.p. 9277 bracket T7 Gene 2. This 512 b.p. fragment was isolated by agarose gel electrophoresis.

The cloning vehicle was prepared from pBR322. The plasmid was digested with Pvu II and Ava I. The large fragment containing the origin was isolated by agarose gel electrophoresis. The flush-ended 512 b.p. T7 fragment DNA was then ligated to the flush end (Pvu II site) of the pBR322 fragment; the Ava I end of this fragment remained free since it had a four base single strand overhand (FIG. 5). The ligation reaction was stopped by heating at 65° C. for 10 min. and the DNA was recovered after precipitation with 2 volumes of ethanol. The pellet was redissolved in the buffer and the solubilized DNA was then digested with Nru I (a unique site in pBR322) which also leaves a flush end.

The cut DNA was run on an agarose gel. Bands in the appropriate linear size range were cut out and isolated. These linear DNA fragments were separately recircularized by ligating the blunt ends together and each was transformed into E. coli 294. Clones from each of the transformations were screened by cutting miniprepped DNA with Kpn I, a unique site within the 512 b.p. fragment region (b.p. 9190 of the T7 genome). One of these transformations yielded a clone which on further inspection proved to contain the 512 b.p. DNA fragment in the orientation shown in FIG. 6. This plasmid was named pRR-2T7-35.

Unnecessary DNA was removed from this plasmid prior to combining gene 2 with T7 Gene 1D. This unnecessary DNA was the pBR322 DNA between the Cla I site and the T7 Kpn I site, and it was removed as follows: pRR-2T7-35 was digested with Cla I and Kpn I, and the large fragment was isolated (heavy line-FIG. 7). This DNA fragment was treated with the Klenow enzyme. In this reaction, the Cla I site was filled in, and the Kpn I site, which has a 3' overhang, was blunt-ended. The two blunt ends were then ligated, and the plasmid DNA was transformed into E. coli 294. The clones were screened by digesting the DNA with the enzyme Hae III. From these clones, pRR-1B2T7 was isolated (FIG. 7).

For the transfer of T7 Gene 2 to the T7 Gene 1D system, Bam HI linkers were inserted into the Nde I site of pRR-1B2T7. This was done as follows: The plasmid was digested with Nde I, and the site was filled in with the Klenow fragment. The filled in site was then treated with calf intestinal alkaline phosphatase (CIAP). 5' phosphorylated Bam HI linkers were ligated into the blunt ends and the ligated DNA was transformed into E. coli 294. The clones were screened by digesting plasmid DNA with Bam HI. pRR-9B2T7 was isolated and used in subsequent T7 Gene 2 experiments (FIG. 8).

T7 Genes 1D and 2, and the lac promoter were combined and cloned into PACYC 184 by the following scheme (FIGS. 9 and 10). p804-RI lac was digested with Pvu II and Bam HI. The lac po containing fragment was isolated by agarose gel elecrophoresis. pRR-1T7-39 was digested with Tth111 I, and the site was filled in with the Klenow reaction. Bam HI was used to remove the T7 Gene 1D containing fragment. After isolation by agarose gel electrophoresis and subsequent ligation to the above prepared p804-RI lac vehicle, the resultant plasmids were transformed into E. coli D1210. Clones were initially screened by looking for the absence of growth on IPTG containing agar plates relative to control plates. From these clones, pRR-1T7 lac 5 was isolated (FIG. 5 center).

pRR-9B2T7 was digested with Pst I and Bam HI. The same enzyme digestions were made in pRR-1T7-lac 5. The fragments containing T7 Genes 1D and 2, respectively, were isolated by agarose gel electrophoresis, ligated together, and transformed into E. coli D1210. Clones were screened by digesting plasmid DNA with Eco RI. From this screen, pRR-1T7G2-lac 7 was isolated (FIG. 9 bottom). The lac po-T7 Gene 1D and 2 Eco RI fragment was digested out of pRR-1T7G2-lac 7 and cloned into the Eco RI site of pACYC 184 and transformed into E. coli D1210, using the PACYC 184 tetracycline resistance marker for selection. The plasmid was designated pAC-1T7G2-78 (FIG. 10).

Cloning the T7 Gene 10 Promoter

The T7 Gene 10 promoter is a strong promoter regulating the synthesis of at least two genes, Genes 10A and 10B, both of which code for T7 bacteriophage head proteins. This promoter is recognized only by T7 RNA polymerase in the E. coli-T7 phage system. The promoter is located at b.p. 22,903 of the T7 genome. This sequence is bracketed by two Nci I sites (b.p. 21, 839 and b.p. 23,192).

When Nci I enzyme was used to digest the T7 genome, a 1353 b.p. fragment was obtained containing the promoter. After isolation by agarose gel electrophoresis, the fragment was further digested with Hinc II and Nde I which gave a 342 b.p. fragment encompassing b.p. 22,622 to b.p. 22,964 of the T7 genome. The Nde I site contains the ATG start codon of gene 10A at b.p. 22,966. This fragment was isolated by polyacrylamide gel electrophoresis and after purification, it was cloned into a pBR322 vehicle digested with Eco RI and Nde I. The Eco RI site was filled in with the Klenow fragment prior to the Nde I reaction (FIG. 11). The ligation mixture was transformed into E. coli D1210. Clones were initially screened by digesting mini-preps with Xba I since there is a unique Xba I site in the T7 342 b.p. fragment between the promoter and the ATG codon at b.p. 22,926. From this screen, pRR-Tϕ10-18 was isolated (FIG. 11).

Connecting the Alpha-2 Interferon Gene with the T7 Gene 10 Promoter

To test the entire expression system, the alpha-2 interferon gene (alpha-2 IFN) was chosen. The T7 Gene 10 promoter was cloned into a derivative of pBTIF 13, which is a pBR322 derivative with the alpha-2 IF gene cloned between the Bam HI/Pvu II sites. It is under the control of the tryptophan promoter which is located between the Eco RI site and the Bam HI site in this plasmid. FIG. 12 illustrates the cloning scheme; the heavy line showing the fragments assembled. pRR-T7ϕ10IF-18 was digested with Nde I, and the site was filled in with the Klenow fragment, followed by a digestion with Pst I and the promoter containing fragment was isolated by agarose gel electrophoresis.

pBTIF-13 was digested with Bam HI, and the site was blunt-ended using Exo VII and the then digested with Pst I and the alpha-2 IF gene containing fragment was isolated by agarose gel electrophoresis. The promoter and IF fragments were ligated and transformed into E. coli D1210. pRR-T7ϕ10-If-2 was isolated (FIG. 12) by screening for a unique Xba I/Bgl II fragment created by the T7 Gene 10 promoter-alpha-2 IF juncture.

Cloning the T7ϕ10IF Fragment to pACYC 184.

The T7ϕ10IF combination was cloned into pACYC 184 as shown in FIG. 13. The fragment is bracketed by two Rsa I sites present in the pBR322 portion of pRR-T7ϕ10IF-2. These sites are located at b.p. 2282 and b.p. 3847 of pBR322. When digested with Rsa I, a blunt-ended fragment approximately 1880 b.p. in length is produced. pACYC 184 was digested with Eco RI and the site was filled in by the Klenow reaction. The ends were then treated with calf intestinal alkaline phosphatase and the vehicle was then ready for ligation with the Rsa I fragment isolated above. E. coli D1210 was transformed with the completed ligation reaction. The clones were screened by restriction analysis with Xba I enzyme. pACYC 184 has a single Xba I restriction site, and since one exists i the T7 promoter region of the Rsa I fragment, two bands were observed using this screen. pAC-ϕ10IF-2 was isolated along with other clones.

Since blunt-ended ligation was used to construct pAC-ϕ10IF-2, two orientations were possible. The screen indicated that both orientations were isolated so the orientation of pAC-ϕ10IF-2 was determined by performing restriction enzyme analysis with Xba I and Bam HI. The T7-ϕ10IF fragment reading direction was oriented in the clockwise direction, as shown in FIG. 13.

Improvement of the Expression of the Mutant T7 RNA Polymerase Gene

After analysis of the production of alpha-2 interferon by the mutant T7 RNA polymerase, improvement in expression was made by treating the Eco RI T7 Gene 1D and 2 fragment of pAC-1T7G2-78 with Bal 31 (FIG. 14). The pBR322 DNA that separated the lac po element from the T7 DNA cloned from pT7-13 was removed in varying amounts by setting up the Bal 31 reaction so that approximately 400 base pairs would be removed from each end of the DNA fragment over a thirty minute period. Samples were taken every five minutes and in this way a pool of fragments was created. After purification of the DNA, the fragments were digested with Bam HI.

The cloning vehicle was prepared by digesting p804-RI lac with Pvu II and Bam HI. The entire pool of flush-ended fragments of varying lengths were joined to the lac promoter. The ligation pool was transformed into E. coli D 1210. The clones were screened by digesting with XmnI and Eco RI. An XmnI restriction site exists 28 b.p. distal to the ATG of the T7 RNA polymerase gene. Therefore, the Eco RI/XmnI fragments created by the ligation of the Bal 31 pool to the lac po were of varying lengths due to the digestion by the Bal 31 enzyme. The clones were classified by the length of this fragment which ranged from 530 b.p. to 260 b.p. Clones were designated pRRB followed by its number in the screen. One dozen clones representing different Eco RI/XmnI fragment sizes were transformed with pAC-ϕ10IF-2(FIG. 13) and tested for alpha-2 interferon production upon induction by IPTG, with the results shown in Table 1.

TABLE 1

Production of Alpha-2 Interferon by Induction of Mutant T7 RNA Polymerase Expression with IPTG

| Post-induction Sample Time (Hrs.) | Alpha-2 IFU/ml Klett Unit* | |
|---|---|---|
| | +IPTG** | −IPTG |
| 0 | 6.6 | 8.3 |
| 1 | 23.6 | 5.0 |
| 2 | 29.6 | 5.7 |
| 3 | 42.1 | 7.7 |
| 4 | 58.5 | 2.7 |
| 5 | 69.6 | 1.8 |
| 6 | 72.7 | 1.8 |

*Average of three samples.
**IPTG was added to a final concentration of 5 mM.

The results shown in Table 1 demonstrate the IPTG-inducible production of alpha-2 interferon by the strain harboring pRRB20. There was a significant increase of interferon activity over the six hour test period in the IPTG-induced culture while the uninduced culture showed no significant increase in interferon activity.

The Eco RI/XmnI fragment representing the nucleotide sequence from the Eco RI site in the lac po region to the XmnI site located 28 b.p. distal to the ATG start codon of the T7 polymerase gene was sequenced to determine the number of nucleotides removed by the Bal 31 digestion. It was determined that base pairs 2219 through 2197 of the intervening pBR322 DNA were removed by the Bal 31 digestion. Therefore, the pBR322 DNA sequence that separates the lac promoter from the T7 DNA in the pRRB20 construction runs from b.p. 2197 to b.p. 2067 of the pBR322 sequence.

Cloning the T7 Gene 10 Promoter/alpha-2 Interferon Fragment into pRRB20

As illustrated in FIG. 15, pRRB20 was digested with Hind III and the site was filed in with the Klenow enzyme. The DNA was precipitated with ethanol, resuspended in the appropriate buffer and treated with calf intestinal alkaline phosphatase. The DNA was isolated by agarose gel electrophoresis.

pRR-T7ϕ10-IF was digested with Rsa I and the promoter/alpha-2 interferon fragment was isolated by agarose gel electrophoresis. The Rsa I fragment was ligated with the pRRB20 plasmid prepared above and the ligated DNA was transformed into E. coli D1210. Clones were screened by digesting mini-preps with Xmn I. After the initial screen, the construction was confirmed and the orientation was determined by digesting the clones with Xba I, a unique site in the T7 promoter, and with Nde I, a unique site in the mutant T7 RNA polymerase gene. From this study, strain pRRB20IF-23 was selected as the prototype.

Testing the pRRB20IF-23 System for Production of Alpha-2 Interferon pRRB-20IF-23 was transformed into E. coli RB 791 and E. coli D1210. Both strains contain a chromosomal lac I$^q$ mutation. Induction experiments were run as described for the one plasmid system above. The cells were grown at 30° C. to cell densities of Klett 200 and then induced with IPTG at a final concentration of 5 mM. At this time, the incubation temperature was raised to 37° C. for the remainder of the experiment. Triplicate 1 ml samples were taken at two hour intervals and a final set of samples were made after continuous incubation overnight (about 20 hours post-induction). The results are shown in Table 2.

TABLE 2

Production of Alpha-2 Interferon in E. coli Strains Harboring p/RRB20IF-23 Upon Induction with IPTG

| E. Coli Strain | Post-induction Sample Time (hrs.) | IFU/ml Klett Unit* | |
|---|---|---|---|
| | | (+) IPTG (5 mM) | (−) IPTG |
| D1210 | 0 | 40.0 | 40.0 |
| | 2 | 32.0 | 22.0 |
| | 4 | 129.0 | 16.0 |
| | 6 | 222.2 | 13.0 |
| | 20 | 578.3 | 15.4 |
| RB791 | 0 | 25.0 | 25.0 |
| | 2 | 80.0 | 23.8 |
| | 4 | 105.8 | 18.9 |
| | 6 | 370.4 | 17.3 |
| | 20 | 213.3 | 6.8 |

*Average of three samples.

Table 2 shows the results of a typical experiment for each strain. The data demonstrate that there was a steady accumulation of alpha-2 interferon in the IPTG induced cells. There was a 38 fold difference in the E. coli D1210 host strain and a 30 fold difference with E. coli RB 791 host strain.

Microbial Deposits

E. coli strain D1210 harboring plasmids pAC-1T7G2-78 and pRR-T7ϕ10IF has been deposited with the American Type Culture Collection, Rockville, Md., and assigned Accession Number 67978. E. coli strain D1210 harboring plasmid pRRB20IF-23 has been deposited with the American Type Culture Collection and assigned Accession Number 67979. Both of these deposits were made under the provisions of the Budapest Treaty on the International Recognition of the Deposit of Microorganisms for the Purpose of Patent Procedure.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A DNA sequence comprising a regulatable promoter operatively linked to a gene encoding a truncated bacteriophage T7 RNA polymerase capable of binding to a T7 promoter and carrying out transcription, which gene comprises a nucleotide sequence corresponding to the sequence of FIG. 16, wherein one or more of nucleotide residues 639 to 706 has been deleted to produce a frame shift which creates a new translation stop codon.

2. The DNA sequence of claim 1 in which only nucleotide residue 639 has been deleted.

3. The DNA sequence of claim 1 in which the promoter is a lac or lambda $P_L$ promoter.

4. The DNA sequence of claim 3 in which the promoter is a lac UV5 promoter.

5. A truncated bacteriophage T7 RNA polymerase which is encoded by the gene of claim 1.

6. The polymerase of claim 5 in which only nucleotide residue 639 of the gene encoding the polymerase has been deleted.

7. The polymerase of claim 5 which is encoded by plasmid pAC-1T7G2-78 or pRRB20IF-23.

8. Plasmid pRR-T7ϕ10IF.

9. A recombinant vector comprising a DNA sequence comprising a regulatable promoter operatively linked to a gene encoding a truncated bacteriophage T7 RNA polymerase capable of binding to a T7 promoter and carrying out transcription, which gene comprises a nucleotide sequence corresponding to the sequence of FIG. 16, wherein one or more of nucleotide residues 639 to 706 has been deleted to produce a frame shift which creates a new translation stop codon.

10. The recombinant vector of claim 7 in which only nucleotide residue 639 has been deleted.

11. The recombinant vector of claim 9 in which the promoter is a lac or lambda $P_L$ promoter.

12. The recombinant vector of claim 11 in which the promoter is a lac UV5 promoter.

13. The recombinant vector of claim 12 which is plasmid pAC-1T7G2-78.

14. The recombinant vector of claim 9 which further comprises a DNA sequence comprising a bacteriophage T7 promoter operatively linked to a gene encoding a desired heterologous polypeptide or protein.

15. The recombinant vector of claim 14 in which transcription of the gene encoding the RNA polymerase and the gene encoding the heterologous polypeptide or protein occurs in the same direction in the vector.

16. The recombinant vector of claim 15 in which transcription of the gene encoding the RNA polymerase and the gene encoding the heterologous polypeptide or protein occurs in opposite directions in the vector.

17. The recombinant vector of claim 16 which is plasmid pRRB20IF-23.

18. A transformed bacterium comprising:
(a) a first DNA sequence comprising a bacteriophage T7 promoter operatively linked to a gene encoding a desired heterologous protein or polypeptide; and
(b) a second DNA sequence comprising a regulatable promoter operatively linked to a gene encoding a truncated bacteriophage T7 RNA polymerase capable of binding to a T7 promoter and carrying out transcription, which gene comprises a nucleotide sequence corresponding to the sequence of FIG. 16, wherein one or more of nucleotide residues 639 to 706 has been deleted to produce a frame shift which creates a new translation stop codon, which bacterium is capable of expressing both the gene encoding the heterologous protein or polypeptide and the gene encoding the polymerase.

19. The transformed bacterium of claim 18 in which only nucleotide residue 639 of the gene encoding the truncated polymerase has been deleted.

20. The transformed bacterium of claim 18 in which the gene encoding the heterologous protein or polypeptide and the gene encoding the polymerase are in two different recombinant vectors.

21. The transformed bacterium of claim 18 in which the gene encoding the heterologous protein or polypeptide and the gene encoding the polymerase are in one recombinant vector.

22. The transformed bacterium of claim 18 which is an E. coli bacterium.

23. The transformed bacterium of claim 22 which contains a lac I$^q$ repressor.

24. A method for producing a desired heterologous protein or polypeptide, comprising:
(a) culturing a transformed bacterium comprising:
(i) a first recombinant vector comprising a DNA sequence comprising a bacteriophage T7 promoter operatively linked to a gene encoding a desired heterologous protein or polypeptide; and
(ii) a second recombinant vector comprising a DNA sequence comprising a regulatable promoter operatively linked to a gene encoding a truncated bacteriophage T7 RNA polymerase capable of binding to a T7 promoter and carrying out transcription, which gene comprises a nucleotide sequence corresponding to the sequence of FIG. 16, wherein one or more of nucleotide residues 639 to 706 has been deleted to produce a frame shift which creates a new translation stop codon,
under conditions in which both the gene encoding the heterologous protein or polypeptide and the gene encoding the polymerase are express; and
(b) recovering the protein or polypeptide from the culture.

25. The method of claim 24 in which only nucleotide residue 639 of the gene encoding the polymerase has been deleted.

26. The method of claim 24 in which the transformed bacterium is an E. coli bacterium.

27. The method of claim 24 in which the protein is recombinant human alpha-2 interferon.

28. A method for producing a desired heterologous protein or polypeptide comprising:
(a) culturing a transformed bacterium comprising a recombinant vector comprising:
(i) a first DNA sequence comprising a bacteriophage T7 promoter operatively linked to a gene encoding a desired heterologous protein or polypeptide; and
(ii) a second DNA sequence comprising a regulatable promoter operatively linked to a gene encoding a truncated bacteriophage T7 RNA polymerase capable of binding to a T7 promoter and carrying out transcription, which gene comprises a nucleotide sequence corresponding to the sequence of FIG. 16, wherein one or more of nucleotide residues 639 to 706 has been deleted to produce a frame shift which creates a new translation stop codon, under conditions in which both the gene encoding the heterologous protein or polypeptide and the gene encoding the polymerase are expressed; and (b) recovering the protein or polypeptide from the culture.

29. The method of claim 28 in which only nucleotide residue 639 of the gene encoding the polymerase has been deleted.

30. The method of claim 28 in which the transformed bacterium is an *E. coli* bacterium.

31. The method of claim 28 in which transcription of the gene encoding the RNA polymerase and the gene encoding the heterologous polypeptide or protein occurs in the same direction in the vector.

32. The method of claim 28 in which transcription of the gene encoding the RNA polymerase and the gene encoding the heterologous polypeptide or protein occurs in opposite directions in the vector.

33. The method of claim 28 in which the protein is recombinant human alpha-2 interferon.

* * * * *